(12) United States Patent
Harding et al.

(10) Patent No.: US 10,898,151 B2
(45) Date of Patent: Jan. 26, 2021

(54) REAL-TIME RENDERING AND REFERENCING FOR MEDICAL PROCEDURES

(71) Applicant: Medtronic, Inc., Minneapolis, MN (US)

(72) Inventors: William C. Harding, Chandler, AZ (US); Martha De Cunha Maluf-Burgman, The Hague (NL); Brian Lee Bechard, St. Paul, MN (US); Michael J. Ferguson, Gilbert, AZ (US); Patrick W. Kinzie, Glendale, AZ (US); Ryan H. Gertenbach, Chandler, AZ (US); Emily Clare Byrne, Tempe, AZ (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 16/176,893

(22) Filed: Oct. 31, 2018

(65) Prior Publication Data

US 2020/0129136 A1    Apr. 30, 2020

(51) Int. Cl.
| | |
|---|---|
| *G06F 3/01* | (2006.01) |
| *A61B 6/00* | (2006.01) |
| *A61B 90/00* | (2016.01) |
| *G06T 19/00* | (2011.01) |

(52) U.S. Cl.
CPC ............... *A61B 6/52* (2013.01); *A61B 6/44* (2013.01); *A61B 6/481* (2013.01); *A61B 6/485* (2013.01); *A61B 6/547* (2013.01); *A61B 90/361* (2016.02); *G06F 3/011* (2013.01); *A61B 6/504* (2013.01); *A61B 2090/365* (2016.02); *G06T 19/006* (2013.01)

(58) Field of Classification Search
None
See application file for complete search history.

(56) References Cited

U.S. PATENT DOCUMENTS

| | | | | |
|---|---|---|---|---|
| 6,847,336 | B1* | 1/2005 | Lemelson | G16H 20/40 345/8 |
| 9,558,587 | B2* | 1/2017 | Kang | G06T 17/20 |
| 9,846,765 | B2* | 12/2017 | Audigier | G06F 19/3481 |
| 2008/0123927 | A1* | 5/2008 | Miga | G06T 7/344 382/131 |
| 2011/0236868 | A1* | 9/2011 | Bronstein | G09B 23/30 434/267 |

(Continued)

*Primary Examiner* — David H Chu
(74) *Attorney, Agent, or Firm* — Holland & Hart LLP

(57) ABSTRACT

Methods, systems, and devices for medical imaging are described. Examples may include an augmented reality (AR) server receiving a set of medical imaging data acquired by at least a first imaging modality. The set of medical imaging data may include a visual representation of a biological structure of a body. Next, the medical imaging data can be used to render an isolated anatomical model of a least a portion of the biological structure. The isolated anatomical model can be received by an AR viewing device such as AR glasses. The AR viewing device may display on a display of the AR viewing device, a first view perspective of the isolated anatomical model in a first orientation. The first orientation may be based on a position of the first AR viewing device relative to the body. Examples include displaying a virtual position of the medical instrument in the AR viewing device.

32 Claims, 21 Drawing Sheets

(56) References Cited

U.S. PATENT DOCUMENTS

| | | | | |
|---|---|---|---|---|
| 2013/0170725 A1* | 7/2013 | Kang | ............... | G06K 9/00362 |
| | | | | 382/131 |
| 2014/0119625 A1* | 5/2014 | Oh | ............... | G06T 7/60 |
| | | | | 382/131 |
| 2014/0277032 A1* | 9/2014 | Ahn | ............... | A61N 7/02 |
| | | | | 606/169 |
| 2015/0051480 A1* | 2/2015 | Hwang | ............... | A61B 8/08 |
| | | | | 600/424 |
| 2016/0004917 A1* | 1/2016 | Yoshida | ............... | A61B 90/36 |
| | | | | 382/115 |
| 2016/0225192 A1* | 8/2016 | Jones | ............... | G06T 19/006 |
| 2016/0364880 A1* | 12/2016 | Barratt | ............... | G06T 7/143 |
| 2017/0255745 A1* | 9/2017 | Mihalef | ............... | G06F 17/11 |
| 2017/0329927 A1* | 11/2017 | Taherian | ............... | A61B 5/055 |
| 2018/0063205 A1* | 3/2018 | French | ............... | H04L 65/1089 |
| 2018/0161012 A1* | 6/2018 | Bang | ............... | A61B 6/4417 |
| 2018/0344411 A1* | 12/2018 | Fahey | ............... | A61B 34/20 |
| 2019/0114802 A1* | 4/2019 | Lazarow | ............... | G06T 7/74 |
| 2019/0231436 A1* | 8/2019 | Panse | ............... | A61B 34/20 |
| 2019/0254754 A1* | 8/2019 | Johnson | ............... | G06T 19/006 |
| 2019/0365498 A1* | 12/2019 | Gibby | ............... | A61B 5/066 |
| 2020/0038119 A1* | 2/2020 | Geri | ............... | G06T 19/003 |

\* cited by examiner

REAL-TIME RENDERING AND REFERENCING FOR MEDICAL PROCEDURES

BACKGROUND

The following relates generally to medical imaging, and more specifically to real-time rendering and referencing for medical procedures.

In medical procedures such as vascular catheterization, cardiac catheterization, neurosurgery, spinal surgery, endoscopic procedures, arthroscopy, laparoscopy, needle biopsy, and other minimally or less invasive surgeries, a physician typically navigates a medical instrument with the assistance of visual aids. In some cases, where larger access ports can be used such as in the abdomen, larger surgical tools may be equipped with cameras to view an internal surgical site. In other cases, where it is desirable to reduce the invasiveness of the procedure, external visualization devices such as radiological images (e.g., X-ray, Fluoroscopy, computed tomography (CT), magnetic resonance imaging (MRI), Ultrasound, or the like) may be used to provided visual information as to where the medical instrument is located within a body.

Medical staff performing radiology guided procedures typical use contrast agents to help visualize patient anatomy. In these cases, a contrast agent may be used with one or more radiological modalities such as Fluoroscopy, to enhance the distinction between an internal structure such as a blood vessel and other surrounding tissue. Accordingly, the person performing the procedure, typically a physician, can view on a monitor the medical instruments located within a patient's body. As the medical instrument is navigated or used in a procedure, the physician may need to take additional radiological images to visualize how a medical device has moved or to determine if the procedure is progressing as desired. For example, a physician placing a cardiac stent may need to take multiple contrast enhanced Fluoroscopy images just to navigate the catheter through a patient's vascular structure to the procedure location. Subsequently, more images may be needed to more precisely position the catheter in the desired location within the blood vessel. Then, as the stent is being deployed from the catheter a physician may take more radiological images to verify correct placement of the stent. Before completing the procedure, additional images may be taken to ensure that the stent is functioning correctly.

Each time a physician needs to visualize what is occurring during a minimally invasive procedure, a patient is exposed to a radiological imaging modality. In some cases, contrast agents are also used to help visualize biological structures such as blood vessels. The repeated radiological imaging of a patient results in increased exposure dosages to ionizing radiation. Further, many contrast agents may be toxic or have other negative health effects on a patient. During the procedure, every time radiological imaging is performed the procedure is stopped. In many cases the radiology machines are large and located at fixed locations relative to a patient. In this regard, radiological images are typically taken from a limited number of viewpoints and displayed on a monitor in different view perspectives from where the physician may be located and or performing the procedure. These factors may combine to increase the time, complexity, and risk of various medical procedures.

SUMMARY

The described features generally relate to methods, systems, devices, or apparatuses that support real-time rendering and referencing for medical procedures.

A method of medical imaging is described. The method may include receiving a set of medical imaging data acquired by at least a first imaging modality, the set of medical imaging data including a visual representation of a biological structure of a body, rendering an isolated anatomical model of at least a portion of the biological structure, and displaying, on a display of an augmented reality (AR) viewing device, a first view perspective of the isolated anatomical model, where the first view perspective displays the isolated anatomical model in a first orientation based on a position of the first AR viewing device relative to the body.

An apparatus for medical imaging is described. The apparatus may include a processor, memory in electronic communication with the processor, and instructions stored in the memory. The instructions may be executable by the processor to cause the apparatus to receive a set of medical imaging data acquired by at least a first imaging modality, the set of medical imaging data including a visual representation of a biological structure of a body, render an isolated anatomical model of at least a portion of the biological structure, and display, on a display of an augmented reality (AR) viewing device, a first view perspective of the isolated anatomical model, where the first view perspective displays the isolated anatomical model in a first orientation based on a position of the first AR viewing device relative to the body.

Another apparatus for medical imaging is described. The apparatus may include means for receiving a set of medical imaging data acquired by at least a first imaging modality, the set of medical imaging data including a visual representation of a biological structure of a body, rendering an isolated anatomical model of at least a portion of the biological structure, and displaying, on a display of an augmented reality (AR) viewing device, a first view perspective of the isolated anatomical model, where the first view perspective displays the isolated anatomical model in a first orientation based on a position of the first AR viewing device relative to the body.

A non-transitory computer-readable medium storing code for medical imaging is described. The code may include instructions executable by a processor to receive a set of medical imaging data acquired by at least a first imaging modality, the set of medical imaging data including a visual representation of a biological structure of a body, render an isolated anatomical model of at least a portion of the biological structure, and display, on a display of an augmented reality (AR) viewing device, a first view perspective of the isolated anatomical model, where the first view perspective displays the isolated anatomical model in a first orientation based on a position of the first AR viewing device relative to the body.

Some examples of the method, apparatuses, and non-transitory computer-readable medium described herein may further include operations, features, means, or instructions for tracking a real-time change in position of the AR viewing device, and displaying a real-time position of the first view perspective of the isolated anatomical model based on tracking the real-time change in position of the AR viewing device.

In some examples of the method, apparatuses, and non-transitory computer-readable medium described herein, displaying the real-time position of the first view perspective of the isolated anatomical model may include operations, features, means, or instructions for updating the first view perspective of the isolated anatomical model based on a change in position of the AR viewing device relative to the body, where updating the first view perspective includes displaying the isolated anatomical model in a second orientation based on the change in position of the AR viewing device.

Some examples of the method, apparatuses, and non-transitory computer-readable medium described herein may further include operations, features, means, or instructions for receiving real-time position data of a medical instrument relative to a reference point of the body.

Some examples of the method, apparatuses, and non-transitory computer-readable medium described herein may further include operations, features, means, or instructions for computing a virtual position of the medical instrument relative to the isolated anatomical model based on the received real-time position data of the medical instrument.

In some examples of the method, apparatuses, and non-transitory computer-readable medium described herein, the computing the virtual position of the medical instrument corresponds to a real-time position of the medical instrument relative to the reference point of the body.

Some examples of the method, apparatuses, and non-transitory computer-readable medium described herein may further include operations, features, means, or instructions for displaying a real-time virtual position of the medical instrument in the first view perspective of the AR viewing device, where the real-time virtual position of the medical instrument may be oriented within the isolated anatomical model based on the received real-time position data of the medical instrument relative to the reference point of the body.

In some examples of the method, apparatuses, and non-transitory computer-readable medium described herein, receiving the real-time position data of the medical instrument further may include operations, features, means, or instructions for receiving signal data from an active tracking component located on the medical instrument.

In some examples of the method, apparatuses, and non-transitory computer-readable medium described herein, the signal data includes at least one of a force measurement, an ultrasonic measurement, a magnetic measurement, an orientation measurement, or a combination thereof.

Some examples of the method, apparatuses, and non-transitory computer-readable medium described herein may further include operations, features, means, or instructions for receiving at least a portion of the real-time position data of the medical instrument from a navigation instrument located outside the body.

In some examples of the method, apparatuses, and non-transitory computer-readable medium described herein, the real-time position data of the medical instrument includes at least one of ultrasonic data, radio frequency identification (RFID) sensor data, contrast imaging data, GPS data, orientation data, or a combination thereof.

Some examples of the method, apparatuses, and non-transitory computer-readable medium described herein may further include operations, features, means, or instructions for determining a medical imaging reference orientation based on receiving the set of medical imaging data, where the medical imaging reference orientation includes position data of the visual representation of the biological structure relative to the body, and displaying an anchoring orientation of the isolated anatomical model within the first view perspective of the AR viewing device, where the anchoring orientation positions the isolated anatomical model to align with the medical imaging reference orientation.

In some examples of the method, apparatuses, and non-transitory computer-readable medium described herein, the anchoring position orients the isolated anatomical model in the first view perspective of the AR viewing device to appear at a location above the body.

Some examples of the method, apparatuses, and non-transitory computer-readable medium described herein may further include operations, features, means, or instructions for updating the first view perspective of the isolated anatomical model in response to a change in position of the AR viewing device, where the updating includes maintaining the isolated anatomical model in the anchoring orientation relative to the body.

Some examples of the method, apparatuses, and non-transitory computer-readable medium described herein may further include operations, features, means, or instructions for receiving a command to change the orientation of the isolated anatomical model from the anchoring orientation to a selected orientation, and displaying, on the display the AR viewing device, a second orientation of the isolated anatomical model, where the second orientation of the isolated anatomical model displays the isolated anatomical model at the selected position based on the position of the AR viewing device relative to the body.

Some examples of the method, apparatuses, and non-transitory computer-readable medium described herein may further include operations, features, means, or instructions for displaying, on a display of a second AR viewing device, a second view perspective of the isolated anatomical model, where the second view perspective displays the isolated anatomical model in a third orientation based on a position of the second AR viewing device relative to the body.

A method of image rendering is described. The method may include receiving a set of imaging data acquired by at least a first imaging modality, the set of imaging data including a visual representation of a structure, rendering an isolated model of at least a portion of the structure, and displaying, on a display of an augmented reality (AR) viewing device, a first view perspective of the isolated model, where the first view perspective displays the isolated model in a first orientation based on a position of the first AR viewing device relative to viewing reference point.

An apparatus for image rendering is described. The apparatus may include a processor, memory in electronic communication with the processor, and instructions stored in the memory. The instructions may be executable by the processor to cause the apparatus to receive a set of imaging data acquired by at least a first imaging modality, the set of imaging data including a visual representation of a structure, render an isolated model of at least a portion of the structure, and display, on a display of an augmented reality (AR) viewing device, a first view perspective of the isolated model, where the first view perspective displays the isolated model in a first orientation based on a position of the first AR viewing device relative to viewing reference point.

Another apparatus for image rendering is described. The apparatus may include means for receiving a set of imaging data acquired by at least a first imaging modality, the set of imaging data including a visual representation of a structure, rendering an isolated model of at least a portion of the structure, and displaying, on a display of an augmented reality (AR) viewing device, a first view perspective of the isolated model, where the first view perspective displays the isolated model in a first orientation based on a position of the first AR viewing device relative to viewing reference point.

A non-transitory computer-readable medium storing code for image rendering is described. The code may include instructions executable by a processor to receive a set of imaging data acquired by at least a first imaging modality, the set of imaging data including a visual representation of a structure, render an isolated model of at least a portion of the structure, and display, on a display of an augmented reality (AR) viewing device, a first view perspective of the isolated model, where the first view perspective displays the isolated model in a first orientation based on a position of the first AR viewing device relative to viewing reference point.

In some examples of the method, apparatuses, and non-transitory computer-readable medium described herein, the structure includes at least a set of internal features that may be contained within the interior of the structure, and the set of imaging data includes a visual representation of at least a portion of the set of internal features.

A method of medical imaging is described. The method may include displaying, in a display device of an augmented reality (AR) viewing device, a first view perspective of an isolated anatomical model in a first orientation based on a position of the first AR viewing device relative to the body, receiving position data of a medical instrument relative to a reference point of the body, where the medical instrument is located within an interior of the body, and displaying a virtual position of the medical instrument in the first view perspective of the AR view device, where the virtual position of the medical instrument is displayed at a relative position to the isolated anatomical model based at least on part on the received position data of the medical instrument.

An apparatus for medical imaging is described. The apparatus may include a processor, memory in electronic communication with the processor, and instructions stored in the memory. The instructions may be executable by the processor to cause the apparatus to display, in a display device of an augmented reality (AR) viewing device, a first view perspective of an isolated anatomical model in a first orientation based on a position of the first AR viewing device relative to the body, receive position data of a medical instrument relative to a reference point of the body, where the medical instrument is located within an interior of the body, and display a virtual position of the medical instrument in the first view perspective of the AR view device, where the virtual position of the medical instrument is displayed at a relative position to the isolated anatomical model based at least on part on the received position data of the medical instrument.

Another apparatus for medical imaging is described. The apparatus may include means for displaying, in a display device of an augmented reality (AR) viewing device, a first view perspective of an isolated anatomical model in a first orientation based on a position of the first AR viewing device relative to the body, receiving position data of a medical instrument relative to a reference point of the body, where the medical instrument is located within an interior of the body, and displaying a virtual position of the medical instrument in the first view perspective of the AR view device, where the virtual position of the medical instrument is displayed at a relative position to the isolated anatomical model based at least on part on the received position data of the medical instrument.

A non-transitory computer-readable medium storing code for medical imaging is described. The code may include instructions executable by a processor to display, in a display device of an augmented reality (AR) viewing device, a first view perspective of an isolated anatomical model in a first orientation based on a position of the first AR viewing device relative to the body, receive position data of a medical instrument relative to a reference point of the body, where the medical instrument is located within an interior of the body, and display a virtual position of the medical instrument in the first view perspective of the AR view device, where the virtual position of the medical instrument is displayed at a relative position to the isolated anatomical model based at least on part on the received position data of the medical instrument.

DETAILED DESCRIPTION

Figure 1:
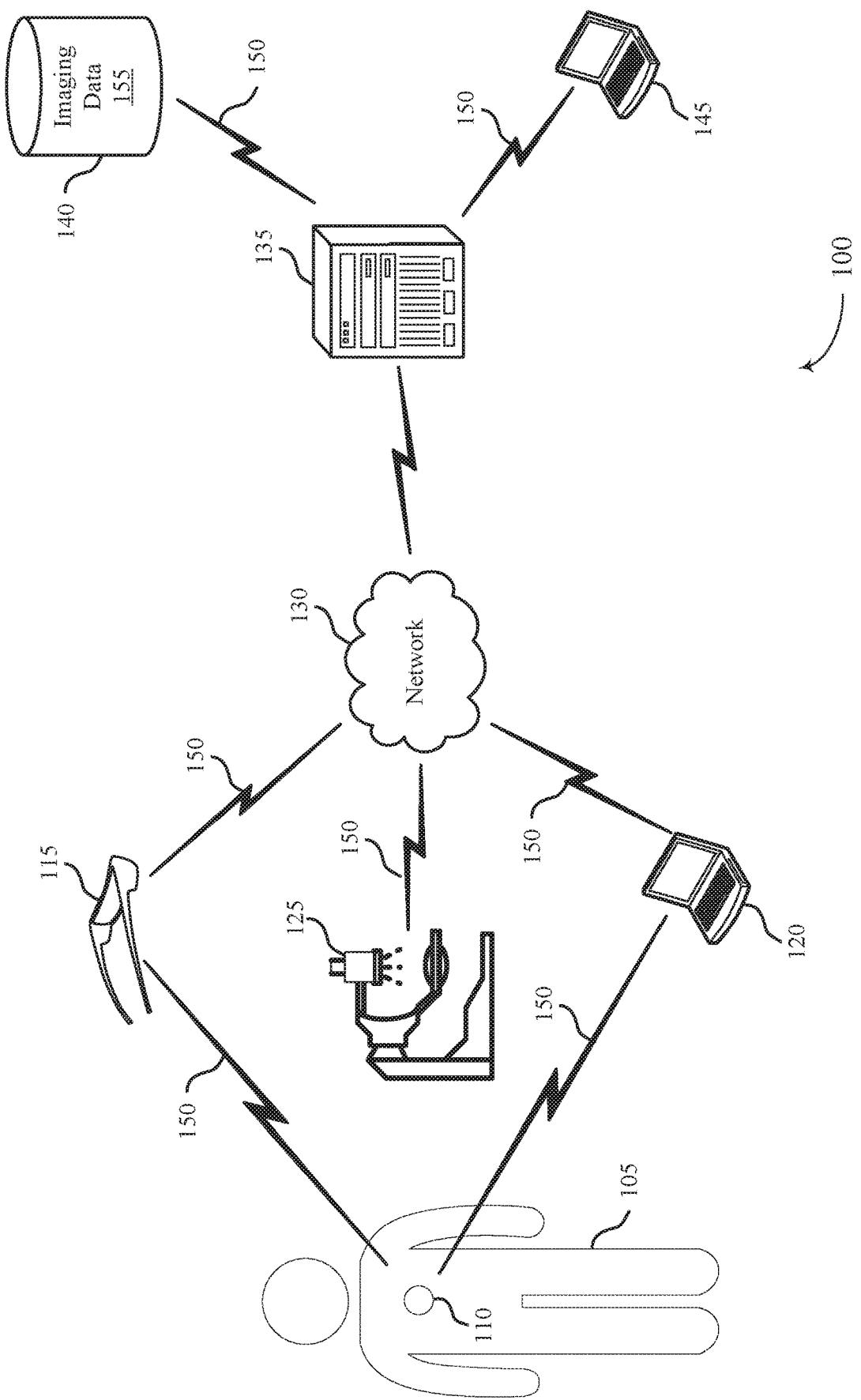
FIG. 1 illustrates an example of a system for medical imaging that supports real-time rendering and referencing for medical procedures in accordance with aspects of the present disclosure.

Aspects of the disclosure include an augmented reality (AR) system that supports visualizing biological structures within the body of a patient. The AR system may include an AR server and AR viewing device (e.g., AR glasses, virtual reality (VR) glasses, AR/VR goggles and headsets, or the like). The AR server may receive a set of medical imaging data acquired by a first imaging modality (e.g., X-ray, Fluoroscopy, CT, MRI. Ultrasound, or the like). The set of medical imaging data may include a visual representation of a biological structure of a body. The AR server may render an isolated anatomical model of at least a portion of the biological structure. In some aspects, this may include isolating part of an organ represented in the set of medical imaging data such a vascular structure from other tissue.

A first view perspective of the isolated anatomical model may be displayed on a display of an AR viewing device. The first view perspective displays the isolated anatomical model in a first orientation based on a position of the AR viewing device relative to the body. For example, this may include a user looking through the AR viewing device to see a first perspective of the body of a patient. The AR viewing device may display the isolated anatomical model above the body. For example, AR viewing device may display a portion of the vascular structure that represents the vascular structure in the patient's body to appear a above the chest of the patient. The isolated anatomical model may be displayed in AR viewing device in a first orientation which may position (rotate, scale, translate, or the like) the isolated anatomical model to align with the biological structure in the patient. For example, this may entail positioning the vascular structure to appear above the chest of the patient's body but otherwise aligned with the vascular structure in the patient's body.

Aspects of the disclosure include tracking a real-time change in position of the AR viewing device as a result of a user moving their head or walking around the body of a patient to change their view perspective relative to the body. In response, AR viewing device may display a real-time position of the first view perspective of the isolated anatomical model based on tracking the real-time change in position of the AR viewing device. For example, this may include updating the first view perspective of the isolated anatomical model based on the change in position of the AR viewing device relative to the body. Updating the first view perspective may include displaying the isolated anatomical model in a second orientation based on the change in position of the AR viewing device. In use, this may include the isolated anatomical model being displayed in a fixed location relative to the body of a patient as a user of the AR viewing device moves or changes their view perspective relative to the patient. As a result, a user wearing VR viewing device and initially looking down at the body may see a top-perspective view of the isolated anatomical model displayed in the AR viewing device. Then, if the user where to crouch down and now be looking up and across the body, they may see a bottom-perspective view of the isolated anatomical model. Accordingly, a user wearing VR goggles may see the body through the goggle and be able to view different portions of the isolated anatomical model by changing their head location and or moving their position relative to the body.

Aspects of the disclosure also include receiving real-time position data of a medical instrument relative to a reference point of the body and computing a virtual position of the medical instrument relative to the isolated anatomical model. The computed virtual position of the medical instrument may correspond to a real-time position of the medical instrument relative to the reference point of the body. The real-time virtual position of the medical instrument may be displayed in the first view perspective of the AR viewing device. In some cases, the real-time virtual position of the medical instrument is oriented within an isolated anatomical model also being displayed in the AR viewing device. As such, a user wearing AR viewing device may view the body of a patient through the device, while a display of the AR device displays a virtual position of the medical instrument relative to the isolated anatomical model. In this regard, the user can view, in the AR viewing device, a representative interaction of the medical instrument with the biological structure that correlates to a procedure being performed within the patient's body.

For example, a physician may be navigating a catheter through a vascular structure in a patient's body. The physician may be able to see the outer surface of the patient's body through the AR viewing device. Further, the AR viewing device may display an isolated anatomical model of a portion of the patient's vascular structure relative to the body, for example suspended above the body. In some examples, the AR viewing device also displays to the physician a virtual position of the medical instrument (e.g., catheter) within the isolated anatomical model (e.g., vascular structure). Accordingly, the physician may have a real-time display of catheterization procedure that is occurring in the body of the patient.

Aspects of the disclosure are initially described in the context of AR systems. Aspects of the disclosure are then described in the context of image rendering techniques. Aspects of the disclosure are also described in the context of a process flow diagram. Aspects of the disclosure are further illustrated by and described with reference to apparatus diagrams, system diagrams, and flowcharts that relate to real-time rendering and referencing for medical procedures.

FIG. 1 illustrates an example of an augmented reality (AR) system 100 in accordance with various embodiments of the present disclosure. The AR system 100 may include a patient 105 undergoing a medical procedure that includes using a medical device 110. Although a single medical device 110 is shown, multiple medical devices 110 may be used during the medical procedure. In some cases, patient 105 may be undergoing a minimally invasive procedure such as a radiological intervention where a catheter or other medical instrument is introduced into the patient's 105 body and guided with the aid of one or more radiology machines 125 (e.g., X-ray, Fluoroscopy, computed tomography (CT), magnetic resonance imaging (MRI), Ultrasound, or the like). In other cases, patient 105 may be undergoing a procedure that involves the use of cameras such as in laparoscopic or endoscopic procedures. Cases also include patient 105 undergoing procedures such as needle biopsies, aspirations, fixture of orthopedic hardware such as the placements of bone screws where a physician or surgeon typical performs the surgery without being able to see portions of the device and relies primarily on experience and feel to complete the procedure.

To assist various medical procedures, radiology machines 125 may be used on a patient to acquire one or more medical images of naturally occurring internal biological structures (e.g., tissue, organs, organ system, blood, other biological system), unnatural biological structures (e.g., cancer, abnormal tissue growth, tumors, implanted engineered biomaterials, or the like), or foreign objects contained within a body (e.g., implanted medical device, sutures, swallowed toys, rocks/pebbles, bullets, or the like), all of which may be referred to generally as biological structures throughout this application. Medical image(s) acquired by one or more radiology machines 125 may provide a visual representation of one or more biological structures in the body of patient 105. Medical images may also include additional data such as patient identification information, information about different parameters used to acquire a medical image or a set of medical images (e.g., exposure levels, attenuation, density, contrast, scatter, radiation dose, frequency, acoustic absorption, acoustic velocity, magnetic field gradients, slice thickness, or the like), information about the location of a body relative to the radiology machine 125, orientation information of the radiology machine 125, calibration information, dimensions of calibration markers used in measurement techniques, or the like. The one or more medical images or other information associated with the medical image(s) may be transferred in suitable formats such as a Digital Imaging and Communications in Medicine (DICOM) format, proprietary or open computer file formats such as those used for word documents, spreadsheets, image files, multimedia formats, or the like.

The one or more radiology machines 125 may use network 130 to transmit the medical images on wired or wireless communication links 150 to an AR viewing device 115, to computing device 120, to AR server 135, to database 140, or to remote computing device 145. Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

The medical images may be further processed at AR viewing device 115, computing device 120, AR server 135, remote computing device 145, or a combination thereof. The one or more medical images may be processed and stored as imaging data 155 at various local or remote databases, at AR viewing device 115, at computing device 120, at augmented reality server 135, at remote computing device 145, or a combination thereof. In some cases, processing medical images to generate imaging data 155 may include isolating specific anatomical features from one or more medical images such as by isolating components of an image that represent a specific organ such as a blood vessel. For example, a medical image acquired using contrast enhancement procedures may display structures in the body based on, for example, absorption of the imaging radiation. In this regard, the blood volume of a blood vessel injected with a contrast agent may appear brightly contrasted to surrounding tissue, which may appear in the medical image as darker structure surrounding the blood volume. From this, the brightly contrasted blood volume may be isolated from the surrounding tissue in the medical image to generate imaging data 155. For example, by removing all aspects of an image below a defined brightness threshold, thereby generating imagining data 155 containing only blood vessel structures that were injected with contrast agent. Such imaging data 155 may include other information from the medical images such as patient data, exposure parameters or other information as described above and may be combined with other imaging data 155 generated from one or more radiology procedures.

In some cases, multiple medical images such as CT scans, MRI scans, Fluoroscopy, three-dimensional (3D) Ultrasound, or the like may be used to generate imaging data 155 that includes 2D or 3D models of biological structures of patient's 105 body. For example, these medical images may be used to generate imaging data 155 that includes 2D or 3D vectorized images or models, 2D or 3D computer graphics such as wireframe models or raster graphics, 2D or 3D computer aided design (CAD) models, 2D or 3D parametric models, surfaces representations such as Non-uniform rational basis spline (NURBS) curves and surfaces, mesh surfaces such as polygon surfaces, point cloud data, or the like for representing the one or more biological structures contained within in the one or more medical images. For example, imaging data 155 including a 3D model can be generated by isolating a specific anatomical structure such as a blood vessel in each of a series of scan planes taken at a series of slice planes that are offset by a slice thickness. The anatomical structure (e.g., blood vessel) from each scan plane can be stitched or otherwise combined to generate a 3D model of the patient's blood vessel. Further, processing, such as vectorizing, smoothing, filtering, surface knitting, parameterizing, surface or volume processing procedures, or a combination thereof can be performed to further refine/modify the imaging data 155.

The medical device 110 may transmit signals via wireless communications links 150 to an AR viewing device 115, to computing device 120, to one or more radiology machines 125, or to a network 130. Medical device 110 may be various devices used in surgical procedures such as radiologically guided medical procedures. Examples of medical device 100 include biopsy instruments such as biopsy needles or biopsy catheters, cardiac or vascular catheters, cannula, laparoscopic instruments such as those used for orthopedic surgery, orthopedic hardware, spine surgery instruments, syringe or needles for injecting various medicine or other compounds, implantable devices such as stents, pacemakers, cardiac/vascular occlusion devices, intrauterine devices, or the like. In some cases, medical device 110 more than one device such as a vascular catheter that is used to deliver a cardiac stent. Medical device 110 may include active components such an active lead catheter, laparoscopic camera, infrared light transmitter or detector, visible light transmitters or detectors, force measurement components, ultrasound transmitter/receiver, mechanical components such as cutters, electro-surgical devices, or combinations thereof. Medical device 110 may also include passive components such as radio-opaque markers, bendable structures, elastic structures, or the like.

Computing device 125 may be one or more a wired or wireless device such as a tablet, cellular phone, personal digital assistant (PDA), a dedicated receiver, or other similar device or a spatially distributed network of devices configured to receive signals from the medical device 110. Computing device 125 may be a wireless laptop computer, a clinician Workstation on Wheels, or a smart hospital bed configured to receive signals from the medical device 110. The computing devices 115 may be in communication with AR server 135 via network 125.

Medical device 110 may also communicate directly with the AR server 135 via network 130. AR server 135 may be one or more cloud computing devices, one or more computing devices located within the hospital or in a remote location, or a combination thereof. AR server 135 may be in further communication with one or more remote computing devices 145 (e.g., cloud computing device), or AR viewing device 115, for example, to distribute processing of the medical images to generate imaging data 155. Additionally or alternatively, data such as medical device 110 data to be transferred between the various devices (e.g., AR viewing device 115, computing device 120, radiology machine 125, AR server 135, remote computing device 135, or database 140). The AR server 135 may also be in communication with various remote databases 140 where the collected patient data may be stored. In some cases, the remote databases 140 include electronic medical records (EMR) applications for storing and sharing patient data.

AR viewing device 115 may be a wireless device such as AR or virtual reality (VR) goggles, glasses, headsets, or other wireless device such as a tablet, cellular phone, personal digital assistant (PDA), a dedicated receiver, or other similar device or a spatially distributed network of devices configured to display computer generated content to a user. The AR viewing device 115 may interface with a user in a variety of ways including the user wearing the AR viewing device on their head similar to glasses, goggles, or headsets. Additionally or alternatively, AR viewing device 115 could connect to a user's body through a harness, belt, or other physical coupling mechanism. In some cases, AR viewing device 115 may have an independent stand that mounts to a structure other than the user, such as a floor or bracket. In this example, AR viewing device 115 may be configured to move with the user through active components (e.g., robotic linkages) or passive components (e.g., static balancing linkages, counterweight linkages, or the like).

AR viewing device 115 may be configured to provide a fully immersive VR experience, which may exclusively or primarily display computer generated content to a user; an AR experience, which may overlay digital information with real-world elements; a mixed reality experience, which may allow a user to interact with and manipulate both physical and virtual items; a combination of these experiences; or transition between VR, AR and mixed reality experiences. AR viewing device may be configured to receive control commands from a user such as audio commands, visual gestures, or inputs from one or more physical devices that interface with AR viewing device 115 such as buttons, knobs, switches, other digital or mechanical device, or a combination thereof.

AR viewing device 115 may also communicate directly with AR server 135 via network 130. AR viewing device 115 may be in further communication with one or more medical devices 110, computing device 120, one or more radiology machines 125, remote computing device 145, or a combination thereof. AR viewing device 115 may transmit and receive data on wired or wireless communication links 150. In some examples, AR viewing device may communicate with AR server 135 to display imaging data 155 to a user.

In accordance with various embodiments, methods and apparatuses are described for real-time rendering and referencing for medical procedures. Methods or apparatuses include generating a 2D or 3D representation of model of a biological structure, such as one or more of the biological structures described herein, to be displayed on an AR viewing device during a surgical procedure to aid visualization or navigation of medical device 110. A procedure may include patient 105 being exposed to a first imaging modality (e.g., X-ray, Fluoroscopy, CT, MRI, ultrasound, or the like) to generate a set of medical imaging data 155. In some cases, the medical imaging procedure may occur as a separate procedure such as patient 105 receiving an X-ray or MRI independently of the surgical procedure involving medical device 105. In other cases, a first imaging modality may be performed on the patient in connection with surgical procedure involving medical device 110. For example, before the surgical procedure involving medical device 110 begins, patient 105 may be in the surgical suite and be exposed to the first imaging modality to generate a set of imaging data 115.

At this stage, the set of medical image data 155 may be generated from medical images that were acquired by at least a first imaging modality (e.g., X-ray, Fluoroscopy, CT, MRI, ultrasound, or the like) carried out on a radiology machine 125 or other visualization device such as a 3D scanner, photographic camera, or combinations thereof. Medical imaging data 155 may include a visual representation of a biological structure in the body of patient 105. For example, medical imaging data 155 may include radiological image data, patient data, exposure data, or other information as described herein. In some aspects, imaging data 155 may include isolated portions of biological structures represented in the one or more medical images, post processing data, user defined components such as a user identified anatomical structures, tissue or organ boundaries/interfaces, or the like.

The methods or apparatuses may further include rendering an isolated anatomical model of at least a portion of the biological structure. In some cases, rendering the isolated anatomical model may be carried out on AR server 135, VR viewing device 115, computing device 120, remote computing device 145, or a combination thereof. The isolated anatomical model may include 2D or 3D representations such a vectorized graphics models, 2D or 3D CAD models, or other 2D or 3D models, representation or visualization graphics as described herein. For example, an isolated anatomical model may include a 3D image with associated scaling data, measurement units, orientation data such as an origin, reference plane, or other information relating the 3D image of the isolated anatomical model to patient 105.

At this stage, a physician may begin a surgical or manically invasive procedure on patient 105, such as a vascular catheterization procedure. A user such as a physician may wear AR viewing device 115 to aid navigation of medical device 110 such as a vascular catheter. In this regard, the physician may be able to view the patient through a display or lens of AR viewing device while the AR viewing device also displays an isolated anatomical model (e.g., 3D model) of a biological structure. For example, the isolated anatomical model may be a 3D representation of the vascular structure that the catheter will be navigated through. In some cases, AR viewing device 115 may take into account the user's position relative to patient 105 and display a first view perspective of the isolated anatomical model (e.g., vascular structure). The first view perspective displays the isolated anatomical model in a first orientation based on a position of the first AR viewing device 115 relative to the body of patient 115. For example, AR viewing device 115 may display isolated anatomical model (e.g., vascular structure) as appearing slightly above the body of patient, while otherwise appearing aligned with the actual vascular structure within patient's 105 body. As a result, the user can view a representation of the vascular structure (isolated anatomical model) in the AR viewing device 115 that represents at least a portion of patient's 105 internal structure (e.g., patient's 105 vascular structure) that would not otherwise be visible to the user. Further, the AR viewing device 115 can display the isolated anatomical model based on the user looking at patient's 105 body.

Figure 2:
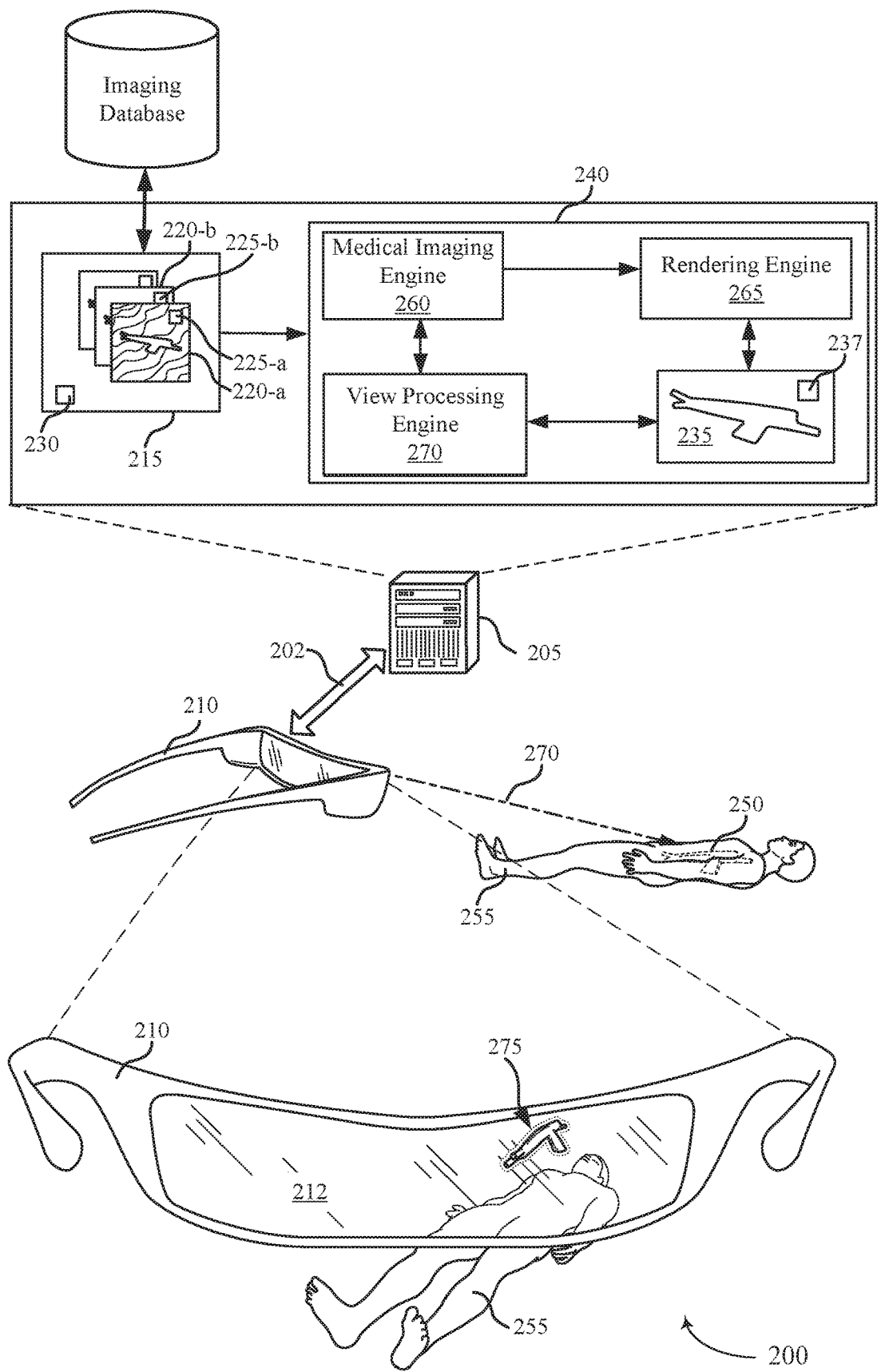
FIG. 2 illustrates an example of an AR system that supports real-time rendering and referencing for medical procedures in accordance with aspects of the present disclosure.

FIG. 2 illustrates an example of an AR system 200 that supports medical device real-time rendering and referencing system in accordance with aspects of the present disclosure. In some examples, AR system 200 may implement aspects of AR system 100. AR system 200 may include an AR server 205 and an AR viewing device 210, which may be examples of AR server 135 and AR viewing device 115 described with reference to FIG. 1. The AR system 200 illustrates an example of a medical imaging procedure where AR server 205 obtains a set of medical imaging data 215, which may be an example of medical imaging data 155 described with reference to FIG. 1. For example, AR server may interface with an imaging database, server, or computational unit such as described herein to acquire imaging data 215 of a body such as a body 255 related to patient 105 described with reference to FIG. 1.

The medical imaging data 215 may be acquired by at least a first imaging modality such as X-ray, Fluoroscopy, CT, MRI, Ultrasound, or other imaging procedure, or a combination thereof. In some aspects, medical imaging data 215 may be acquired using a contrast agent to increase contrast of certain biological structures acquired by one or more imaging modalities. The set of medical imaging data 215 may include a visual representation 220 of a biological structure 250 of a body 255.

Medical imaging data 215 may also include image parameters 225 obtained in relation to one or more imaging modalities. For example, first visual representation 220-*a* may be acquired via X-ray and first image parameters 225-*a* may include patient identification information, scaling information, contrast information, attenuation, scatter, or the like. Further imaging parameters 225 may include addition information such as information entered by medical providers or visual information appended to the image such as overplayed measurements, calibration data, organ/tissue boundaries, interfaces of different tissue, or the like. Such imaging parameters 225 may be manually entered or detected using automated software, or a combination of human and software interaction. In some cases, medical imaging data 215 may include multiple visual representations 220. For example, a second visual representation 220-*b* may be acquired by the same or different imaging modality as first visual representation 220-*a*. Second visual representation 220-*b* may also include second imaging parameters 225-*b*, which may be the same or different from the first imaging parameters 225-*a*.

Imaging data 215, may also include scan data 230 for multiple visual representations 220, which may provide information that relates one or more of visual representation 220 to each other. That is, scan data 230 may include information relating first visual representation 220-*a* and second visual representation 220-*b*. In one example, visual representations 220 could be acquired by a CT scan and scan data 230 could include slice thickness, patient position data, exposure data, or the like. In other examples, visual representations 220 could be acquired by multiple imaging modalities such as MRI and Fluoroscopy. In this case, scan data 230 could include information correlating the MRI data to the Fluoroscopy data for purposes such as alignment of the images, combination of the images, imagining parameters (e.g., contrast, scatter, magnetic field data, etc.), contrast data, combinations thereof, or the like.

Biological structure 250 represented in imaging data 215 may include naturally occurring internal biological structures (e.g., tissue, organs, organ system, blood, other biological system), unnatural biological structures (e.g., cancer, abnormal tissue growth, tumors, implanted engineered biomaterials, or the like), or foreign objects contained within a body (e.g., implanted medical device, sutures, swallowed toys, rocks/pebbles, bullets, or the like), or combinations thereof. In some cases, biological structure 250 may be located internal to body 255. In this regard, biological structure 250 may not be readily visualized by a person observing body 155. For example, biological structure 250 may include organs such as the heart, brain, blood vessels, lungs, gastro-intestinal tract, components of the skeletal system, muscle, boundaries between various anatomical structures such as muscle boundary planes or abdominal walls, other tissue structures, or various combinations thereof. Biological structure 250 may also include portions of the above-mentioned anatomical features, such as a portion of the vascular system represented within imaging data 215.

AR server 205 may include an AR builder module 240, which renders an isolated anatomical model 235 of at least a portion of biological structure 250. AR builder module 240 may include medical imaging engine 260, rendering engine 265, and view processing engine 270. Implementations include medical imaging engine 260, which may receive the set of medical imaging data 215 as described herein. Medical imaging engine 260 may interface with rendering engine 265 and view processing engine 270 to process medical imaging data 215. Rendering engine 265 may process or modify medical imaging data 215 to generate isolated anatomical model 235. In this regard, isolated anatomical model 235 may be a 2D or 3D graphical model that can be displayed in AR viewing device 210, and include scaling information, orientation information, display properties and other information for interfacing with AR viewing device 210 as described herein.

View processing engine 270 may interface with medical imaging engine 260 and isolated anatomical model 235 to support displaying isolated anatomical model 235 on a display 212 of AR viewing device 210. In some cases, AR server 205 establishes a communications link 202 with AR viewing device 210. Data transmission may occur on communications link 202, for example, via wireless transmission frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

AR viewing device 210 may show a first view perspective 270 of isolated anatomical model 235 on display 212. In this regard, the first view perspective 270 may display the isolated anatomical model 235 in a first orientation 275 based on the position of the AR viewing device 210 relative to body 255. For example, in first view perspective 270, AR viewing device 210 may be located above body 255 and looking downward from the feet of body 255 as shown in FIG. 2. In this case, a user may be able to see body 255 through display 212 of AR viewing device 210. Additionally, AR viewing device 210 may determine its relative position to body 255 and show isolated anatomical model 235 on display 212 at first orientation 275 appearing in relation to body 255. For example, AR viewing device 210 may include sensors, interface with computing devices (e.g., computing device 125, remote computing device 145), interface with AR server 205, interface with sensors positioned in the operating room or on body 255, or a combination thereof to determine its relative position within the operating room or relative to body 255. Based on AR viewing device 210 determining its position based on view perspective 270, AR viewing device can use isolated anatomical model data 237 such as orientation data relating the position of the anatomical model 235 to body 255, or scaling information that provides relative dimensions of isolated anatomical model 235 relative to body 255 to position and display isolated anatomical model 235 in first orientation 275. For example, first orientation 275 may display isolated anatomical model to appear above body 255 while otherwise having the same scale and alignments as biological structure 250 has relative to body 255.

AR system 200 may support viewing of biological structures during medical procedures such as minimally invasive radiological guided procedures. For example, a user such as an interventional radiologist may wear VR viewing device 210 during a radiological procedure. In the surgical suite, the VR viewing device 210 may determine its relative location and orientation to body 255 of a patient as well as other objects in the room such as the procedure table based on where the radiologist is positioned. In this example, AR viewing device 210 may receive isolated anatomical model 235 including isolated anatomical model data 237 from AR server over communications link 202. Radiologist may look through display 212 of AR viewing device and see body 255 of the patient. However, radiologist will only be able to see surface features of the patient's body 255. In this regard, radiologist may view isolated anatomical model 235 on display 212 of AR viewing device 210. The AR viewing device may display first orientation 275 of isolated anatomical model 235 in display 212 based on the radiologist's view perspective such as view perspective 270. Accordingly, radiologist is able to view a 2D or 3D representation of a biological structure 250 within body 255 of patient. Moreover, first orientation 275 of isolated anatomical model 235 may be aligned to biological structure 250, which may provide an intuitive view to a radiologist wearing AR viewing device.

A radiologist wearing using AR system 200 is provided purely as one example of processes and capabilities of AR system 200. Accordingly, AR system 200 can be used by other medical professionals such as nurses, technical staff, researchers, or other physicians. Moreover, the use of AR system 200 within the medical field is provided as way illustration, and AR system 200 could be used in non-medical applications where a user may not be able to view an internal structure or have limited view of the internal structure in which they may be trying to navigate or work on. For example, AR system 200 could be used in automotive repair, plumbing, assembly of multipart devices, for navigating pipe structures, etc.

Figure 3:
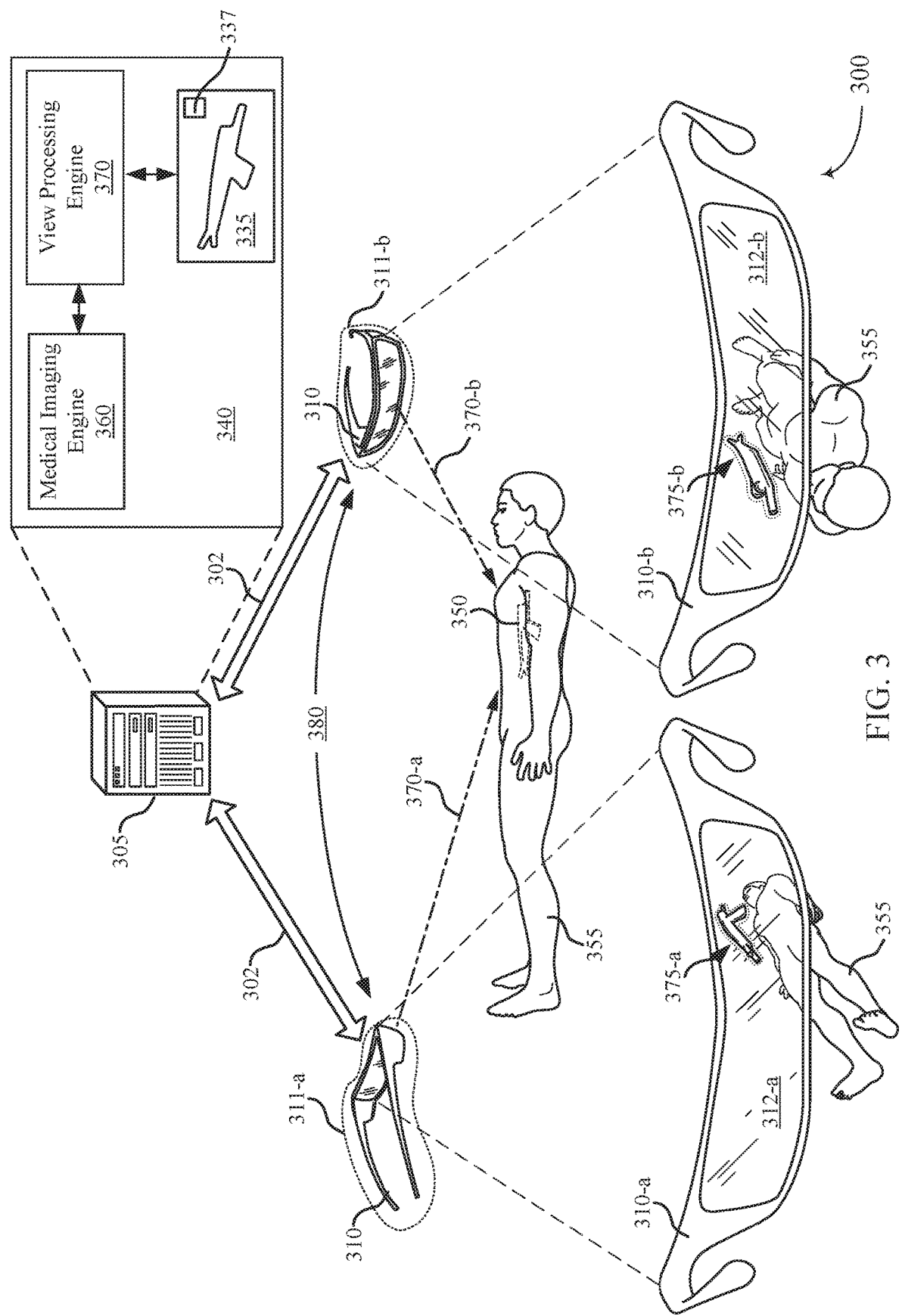
FIG. 3 illustrates an example of an AR system that supports real-time rendering and referencing for medical procedures in accordance with aspects of the present disclosure.

FIG. 3 illustrates an example of an AR system 300 that supports medical device real-time rendering and referencing system in accordance with aspects of the present disclosure. In some examples, AR system 300 may implement aspects of AR systems 100 or 200 described with reference to FIGS. 1 and 2. AR system 300 may include AR server 305 running AR builder module 340, which may be an example of AR builder module 205 described with reference to FIG. 2. AR system 300 may also include AR viewing device 310, which may be an example of AR viewing device 115 or 210 descried with reference to FIGS. 1 and 2. AR system 300 may be implemented to interface with body 355 of a patient having biological structure 350, which may be an example of body of patient 105 described with reference to FIG. 1 or body 255 and biological structure 250 described with reference to FIG. 2.

AR system 300 may support displaying a real-time position of isolated anatomical model 335 in AR viewing device 310 based on a change in position 380 of AR viewing device 310. While being worn by a user, AR viewing device 310 may be in a first position 311-a having a first view perspective 370-a of body 355. The user may move to a new location, thereby causing AR viewing device 310 to undergo a change in position 380 to a second position 311-b having an updated first view perspective 370-b of body 355.

VR system 300 may track a real-time change in position 380 of AR viewing device 310, for example, from first position 311-a to second position 311-b. In some cases, VR viewing device 310 may transfer data with AR server 305 via communications link 302 which may be an example of communications link 202 described with reference to FIG. 2. VR viewing device 310 may determine its change in position 380 relative to body 355 independently such as through on-board sensors (e.g., accelerometers, gyroscope, magnetic field, orientation, rotation, force, light, GPS, range, or the like), with the aid of sensors located within the operating room that body 355 is located in, based on sensors located on body 355, using data from AR server 305, or a combination thereof. AR viewing device may communicate or receive tracking data with AR server 305 via communications link 302.

VR system 300 may further display a real-time position of first view perspective 370 of isolated anatomical model 335 based on tracking the real-time changing in position 380 of AR viewing device 310. In some cases, displaying a real-time change position of first view perspective 370 includes updating first view perspective 370 of isolated anatomical model 335 based on change in position 380 of AR viewing device 310 relative to body 355. For example, when AR viewing device 310 is located at first position 311-a, AR builder module 340 may provide AR viewing device 310 with isolated anatomical model 335 and isolated anatomical model data 337 that supports AR viewing device 310 displaying isolated anatomical model on display 312 in a first orientation 375-a. First orientation 375-a may be shown in display 312 based on first view perspective 370-a such as was described in relation to FIG. 2. In the illustrated example, first orientation 375-a displays isolated anatomical model 335 in a position slightly above the chest of body 355 while otherwise aligned relative to body 355 in the same orientation as biological structure 350.

After change in position 380, AR viewing device may by in second position 311-b having an updated first view perspective 370-b. As illustrated, AR viewing device may be viewing body 355 from the head looking downward toward the feet in the second position 311-b. Based on updated first view perspective 370-b, AR viewing device may display, on AR viewing device 310 display 312, isolated anatomical model 335 in a second orientation 375-b. Second orientation 375-b may be shown in display 312 based on updated first view perspective 370-b. For example, as illustrated, second orientation 375-b displays isolated anatomical model 335 in a position slightly above the chest of body 355 while otherwise aligned relative to body 355 in the same orientation as biological structure 350. That is, a user looking through AR viewing device 310 from second position 311-b would see a different view of isolated anatomical model 335 as compared to when the user was viewing isolated anatomical model from first position 311-a. In the illustrated example, user viewing body 355 from first position 311-a would see isolated anatomical model 335 on display 312 overlaid on body 355 in first orientation 375-a. After user moves causing AR viewing device 310 to change position 380 to second position 311-b, the user now viewing body 355 from second position 311-b would see an updated first view perspective 370-b showing isolated anatomical model 335 on display 312 overlaid on body 355 in second orientation 375-b.

AR viewing device may receiving isolated anatomical model 335, isolated anatomical model data 337, or a combination thereof from AR server 305 over communications link 302. In some cases, AR viewing device 310 may, independently track a real-time change in position 380 without needing to rely on AR server 305. In other cases, AR viewing device 310 may transfer data over communications link 302 indicating a change in position 380. In this regard, AR builder module 340 may employ medical imaging engine 360 and view processing engine 370 to provide updated isolated anatomical model 135 orientation information, scaling information, or the like to AR viewing device 310 for generating updated first view perspective 370 as described herein.

Implementations include, AR server and AR viewing device transferring data over communications link 302 to generate a real-time view of isolated anatomical model 335 in display 312. For example, as a user, wearing AR viewing device 310 walks around body 355, orientation 375 of isolated anatomical model 335 would appear to continuously change within display. This can be implemented in a variety of ways, including isolated anatomical model 335 appearing to remain in a static position relative to body 355, such that as AR viewing device 310 changes position, a user wearing AR viewing device 310 would see different perspectives of isolated anatomical model 335. For example, a physician viewing body 355 of a patient through AR viewing device 310 may initially see a top perspective such as first orientation 375-a overlaid on body 355. Then, the physician may crouch down to change the position of AR viewing device 310 relative to body 355. As a result, the physician may see in display 312 a second orientation 375-b showing different aspects of isolated anatomical model 335. Such real-time tracking of AR device 310 and real-time display of a represented biological feature (e.g., isolated anatomical model 335) may help a physician see different perspectives of the biological feature simply by moving her or his head to change the position of AR viewing device 310.

Figure 4:
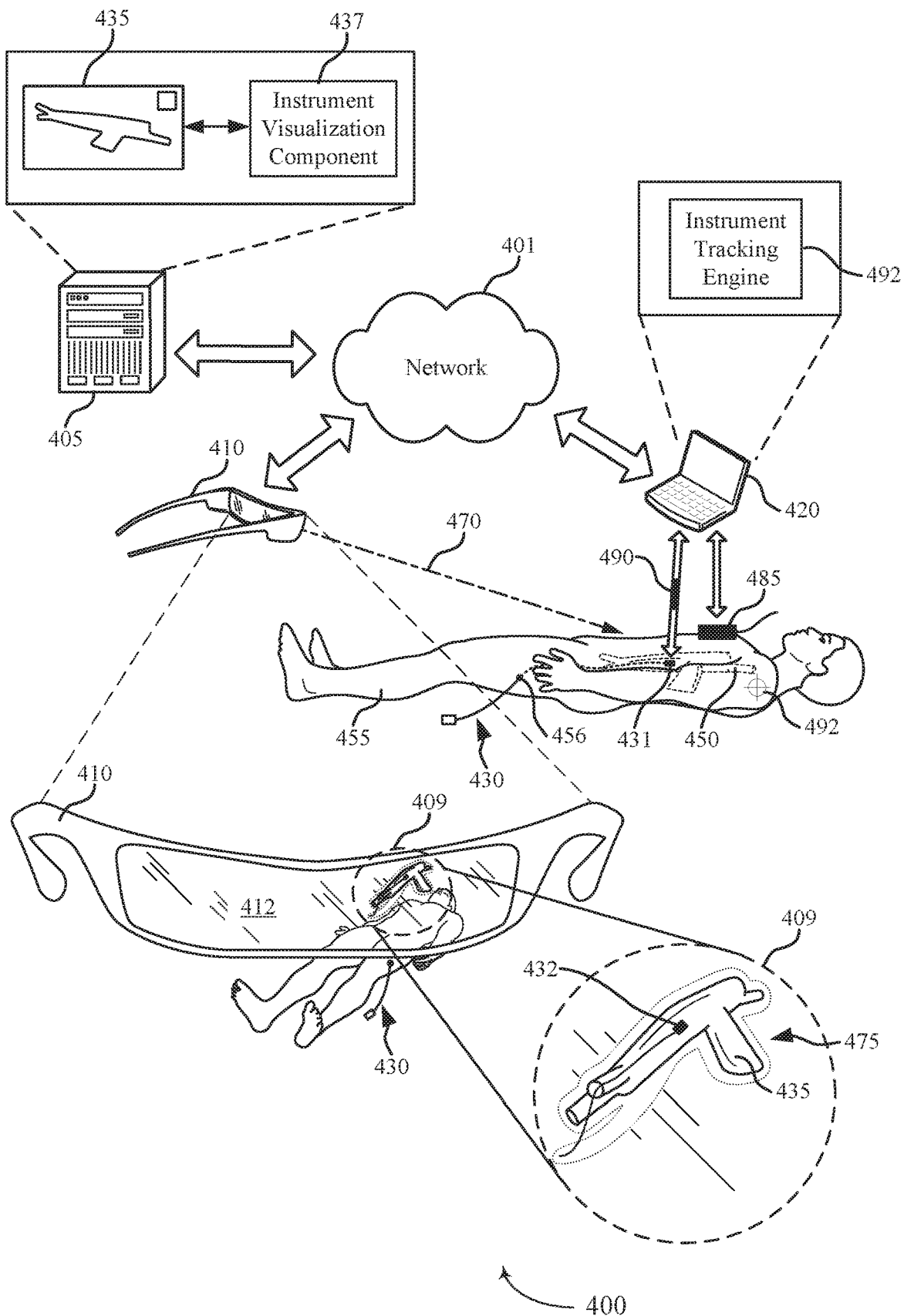
FIG. 4 illustrates an example of an AR system that supports real-time rendering and referencing for medical procedures in accordance with aspects of the present disclosure.

FIG. 4 illustrates an example of an AR system 400 that supports medical device real-time rendering and referencing system in accordance with aspects of the present disclosure. In some examples, AR system 400 may implement aspects of AR systems 100, 200, or 300 described in reference to FIGS. 1, 2, and 3. AR system 400 may include AR server 405, which may be an example of AR servers 135, 205, or 305 describe herein, AR viewing device 410, which may be an example of AR viewing devices 115, 210, or 310 described herein, network 401, which may be an example of Network 135 described herein, and computing device 420, which may be an example of computing device 120 described herein. Further, AR system 400 may include medical instrument 430, which may be an example of medical device 110 described in relation to FIG. 1. Some implementations may also include external tracking device 485.

AR system 400 may include using VR viewing device 410 to aid navigation or use of medical instrument 430 during a medical procedure. As described in relation of FIGS. 1, 2, and 3, a user may wear AR viewing device 410 while performing a medical procedure on body 455. AR viewing device 410 may view body from a first view perspective 470 and display isolated anatomical model 435 on display 412 in a first orientation 475 based on first view perspective 470 relative to body 455. A user, such as a physician may be performing a minimally invasive procedure on body 455 using medical instrument 430 such as a vascular catheter. Medical instrument 430 may be introduced into body 455 at an introduction site 456. Once medical instrument 430 is inserted into introduction site 456, the physician can no longer see the portion of medical instrument 430 that has been inserted into body 455.

In typical minimally invasive cardiac procedures, the physician relies on imaging modalities such as Fluoroscopy to visualize medical instrument within body 455. This may entail, injecting a vessel with a contrast agent using medical instrument and subjecting the patient to radiation to generate images of the vascular structure. In typical procedures such Fluoroscopy guided catheterization, the physician only receives one to few images of a patient's vascular structure during each imaging application. Accordingly, the physician must navigate medical instrument without being able to visualize in real-time where the medical instrument is located relative to a patient's biological structures, such as where a catheter is located within the patient's vascular structure. The static or semi-static (e.g., few second snapshots) Fluoroscopy information typically results in the physician needing to repeatedly image the patient to determine where the catheter is located. As such, the patient is exposed to multiple doses of radiation throughout a procedure. Additionally, repeated imaging slows down the procedure because a physician may have to frequently stop advancing a medical instrument to take more Fluoroscopy images. Moreover, radiological imaged such as Fluoroscopy are displayed on a screen, typically in different perspectives from the physician's orientation to the patient. Accordingly, the physician may need to mentally translate Fluoroscopy views, which are in a different view plane from the physician, into how the catheter may move within the patient's vascular system. Often, these complexities result in damage to patient tissue due to medical instruments colliding with internal structures, extended procedure times, increased radiation doses and suboptimal placement or navigation of medical instruments.

AR system 400 may include tracking a medical instrument 430 within body of patient 455 and displaying a virtual position 432 of medical instrument 430 relative to isolated anatomical model 435 in display 412 of AR viewing device 410. In some cases, the virtual position 432 of medical instrument 430 and isolated anatomical model 45 may be displayed in AR viewing device 410 based on first view perspective 470. According, a user of AR viewing device 410 may see a representation of medical instrument 430 within biological structure 450 from the same perspective that the user is viewing body 455 and performing a medical procedure.

AR system 400 may include computing device 420 receiving a real-time position data 490 of medical instrument 430 relative to a reference point 492 of body 455. In some cases, real-time position data may include receiving a signal from an active tracking component 431 located on medical instrument 430. Examples of signals include signal data correlating to a force measurement, an ultrasonic measurement, a magnetic measurement, an orientation measurement, or a combination thereof. In other examples, real-time position data 492 may include ultrasonic data, radio frequency identification (RFID) sensor data, contrast imaging data, global positioning system (GPS) data, orientation data, or a combination thereof.

Reference point 492 may be implemented in a variety of ways. In a first set of examples, reference point 492 could include one or biological structures such as biological structure 450 within body 455. In some cases, medical instrument 430 could include active components such as an active lead catheter to detect or visualize surrounding tissue of biological structure 450. In this regard, biological structure 450 detected by, for example, an active lead of medical instrument 430, could be matched or correlated to corresponding structure within isolated anatomical model 435. As a result, aspects or portions of biological structure could be used as reference point 492.

In another set of examples, reference point 492, could be an external tracking device 485 located outside or on body 455. In some cases, reference point 492 may include one or more radio frequency identifiers (RFIDs) disposed on body 45 or within the surgical room where body 455 is located. Additionally, or alternatively, external tracking device 485 could be an imaging modality such as ultrasound or X-ray. In yet other examples, reference point could include a combination of internal and external mechanisms. For example, reference point 492 could include distance measurements located on medical instruments 430 that could either be visualized by a user or detected by other means such as magnetic fields, machine vision, digital measurement techniques or the like. In some cases, computing device 420 may include an instrument tracking engine 492. Instrument tracking engine 492 may be configured to process real-time position data 490 received from medical instrument 430, process data received from external tracking device 485 or a combination thereof.

In some aspects, computing device 420 and instrument tracking engine may communicate with AR server 405 over network 401. In other instances, computing device may be combined with AR server 405. In yet other cases, computing device 420 and instrument tracking engine could be combined with or included in AR viewing device 410.

Instrument tracking engine 492 may interface with AR server 405 to compute a virtual position 432 (shown in magnified detailed view 409) of medical instrument 430. For example, real-time position data 490 received from medical instrument 430 or external tracking device 485 may be used to compute virtual position 432 relative to isolated anatomical model 435. In some cases, computing virtual position 432 may be done in real-time. In this regard, real-time virtual position 432 corresponds to a real-time position of medical instrument 430 relative to reference point 492 of body 455.

A virtual position 432 may be displayed on AR viewing device 410 display 412 relative to isolated anatomical model 435. For example, Instrument visualization component 437 may generate a virtual position 432 of medical instrument 430 to be shown on display 412. In some cases, virtual position 432 may be a 2D or 3D model or graphic that provides a visual representation of medical device to a user of AR viewing device 410. In some cases, virtual position 432 of medical instrument 430 may be shown on display 412 to align with first orientation 475 of isolated anatomical model 435 based both on first view perspective 470 and real-time position data 490 of medical instrument relative to reference point 492 of body 455. For example, displaying virtual position 432 in display 412 includes orienting virtual position 432 relative to isolated anatomical model 435 based on the orientation of medical instrument 432 relative to biological structure 450.

Figure 5:
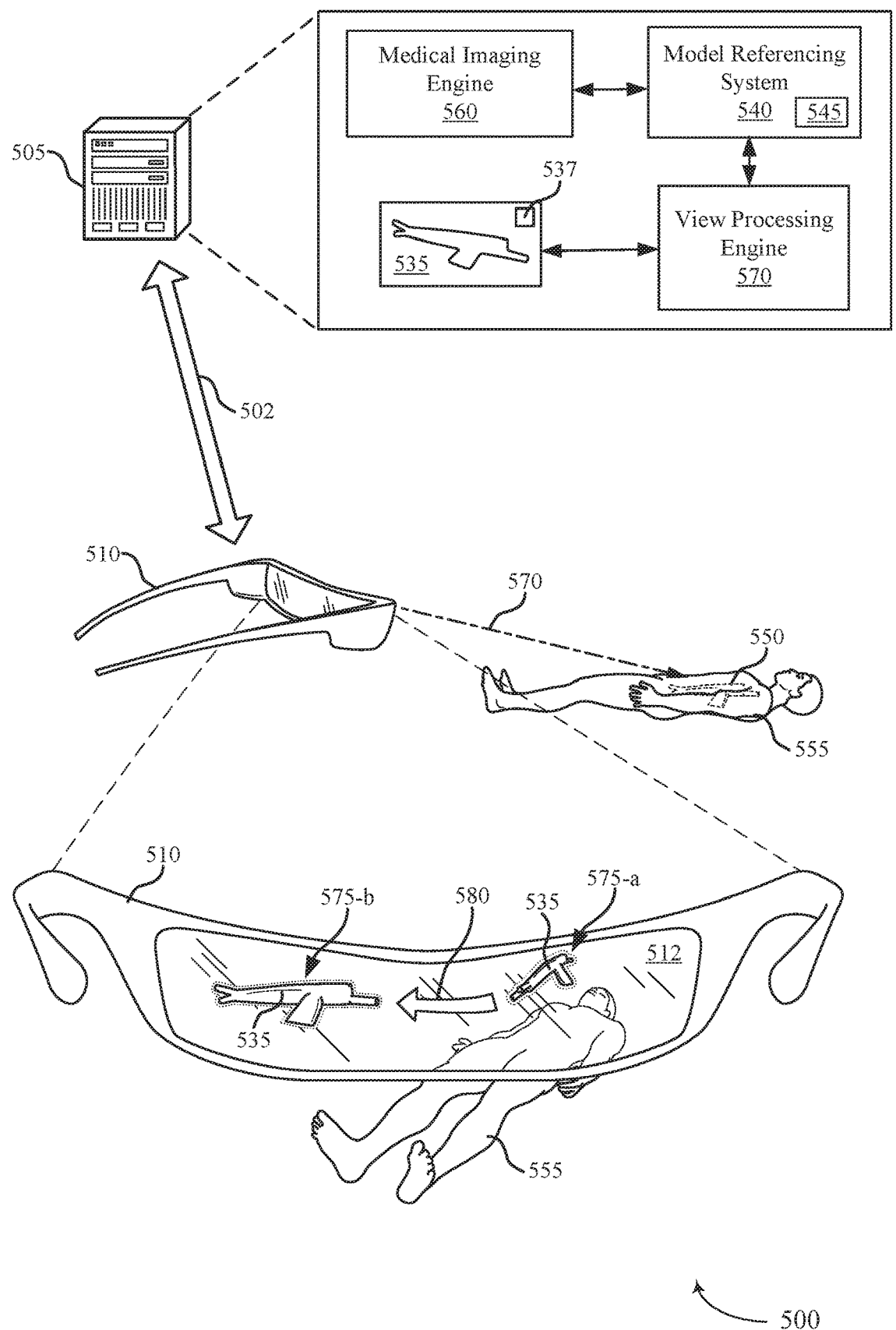
FIG. 5 illustrates an example of an AR system that supports real-time rendering and referencing for medical procedures in accordance with aspects of the present disclosure.

FIG. 5 illustrates an example of an AR system 500 that supports medical device real-time rendering and referencing system in accordance with aspects of the present disclosure. In some examples, AR system 500 may implement aspects of AR systems 100, 200, 300, or 400 described in reference to FIGS. 1, 2, 3, and 4. AR system 500 may include AR server 505, which may be an example of AR servers 135, 205, 305, or 405 described herein, VR viewing device 510, which may be an example of VR viewing devices 115, 210, 310, or 410 described herein, and isolated anatomical model 535, which may be an example of isolated anatomical models 235, 335, or 435 described herein.

AR system 500 may be configured to display isolated anatomical model 535 at different view orientations 575 in display 512 relative to body 555. In some cases, displaying isolated anatomical model 535 at different view orientations 575 may be in response to commands from a user of AR viewing device 510. In this regard, the model referencing system 540, may receive medical imaging data such as medical imaging data 155 and 215 described herein form medical imaging engine 560. Model referencing system 540 may determine a medical imaging reference orientation 545 based on the medical imaging data. The medical imaging reference orientation 545 may contain information about the orientation, size, scale, position data, or the like of biological structure 550 relative to body 555. For example, medical imaging reference orientation 545 may be generated from medical imaging data acquired from one or more imaging modalities (e.g., X-ray, Fluoroscopy, CT. MRI, Ultrasound, or the like) and contain information about the alignment, orientation, scale, size, or the like of one or more medical images included in the medical imaging data.

AR viewing device 510 may receive isolated anatomical model 535 along with isolated anatomical model data 537, which may include orientation information for displaying isolated anatomical model 535 in display 512. AR viewing device 510 may display isolated anatomical model on display 512 in an anchoring orientation 575-a. In some examples, displaying isolated anatomical model 535 in anchoring orientation 575-a includes orienting or positioning the isolated anatomical model 535 based on first view perspective 570 of AR viewing device 510 relative to body. The anchoring orientation 575-a may include positioning (e.g., rotating, aligning, scaling, or the like) isolated anatomical model 535 to align with the medical imaging reference orientation 545. In this regard, isolated anatomical model 535 may be shown on display 512 in the first perspective to be located above the chest of body 555, but otherwise have the same alignment, scale, or other orientation features as biological structure 550 has relative to body 555. That is, in this example isolated anatomical model 535 would appear to a user of AR viewing device 510 in the same orientation relative to body 555 as biological structure 550 is oriented relative to body 555.

In some cases, in anchoring position 575-a, display 512 may show isolated anatomical model 535 location above body 555, while otherwise having the same alignment to body 555 as biological structure 550 has relative to body 555. Such an orientation may facilitate a user having an unobstructed view of isolated anatomical model 535 that is intuitively (e.g., positioned similar to biological structure 550) relative to body 555. Some cases involve maintaining the isolated anatomical model 535 in anchoring orientation relative to body 555 in response to updating first view perspective 570, such as when VR viewing device 510 changes positions as described herein.

VR viewing device 510 may receive a command such as from a user, or from VR server 505 through communications link 502 to change the orientation of the isolated anatomical model 535 from the anchoring orientation 575-*a* to a selected position within display 512. For example, the command may specify a position change 580 from anchoring orientation 575-*a* to a selected orientation 575-*b*. In some examples the position change 580 may include repositioning (rotate, translate, scale, or the like), changing other view properties such as contrast, color, opacity, brightness, surface characteristic, or the like of isolated anatomical model 535. In response to position change 580 command, AR viewing device 510 may display, on display 512 selected orientation 575-*b* of isolated anatomical model. In some cases, selected orientation 575-*b* is based on the position of AR viewing device 510 relative to body 555. For example, second orientation may rotate isolated anatomical model 535 about a central axis, moment of inertia, while maintaining that rotating point in a fixed location relative to body 555.

Figure 6:
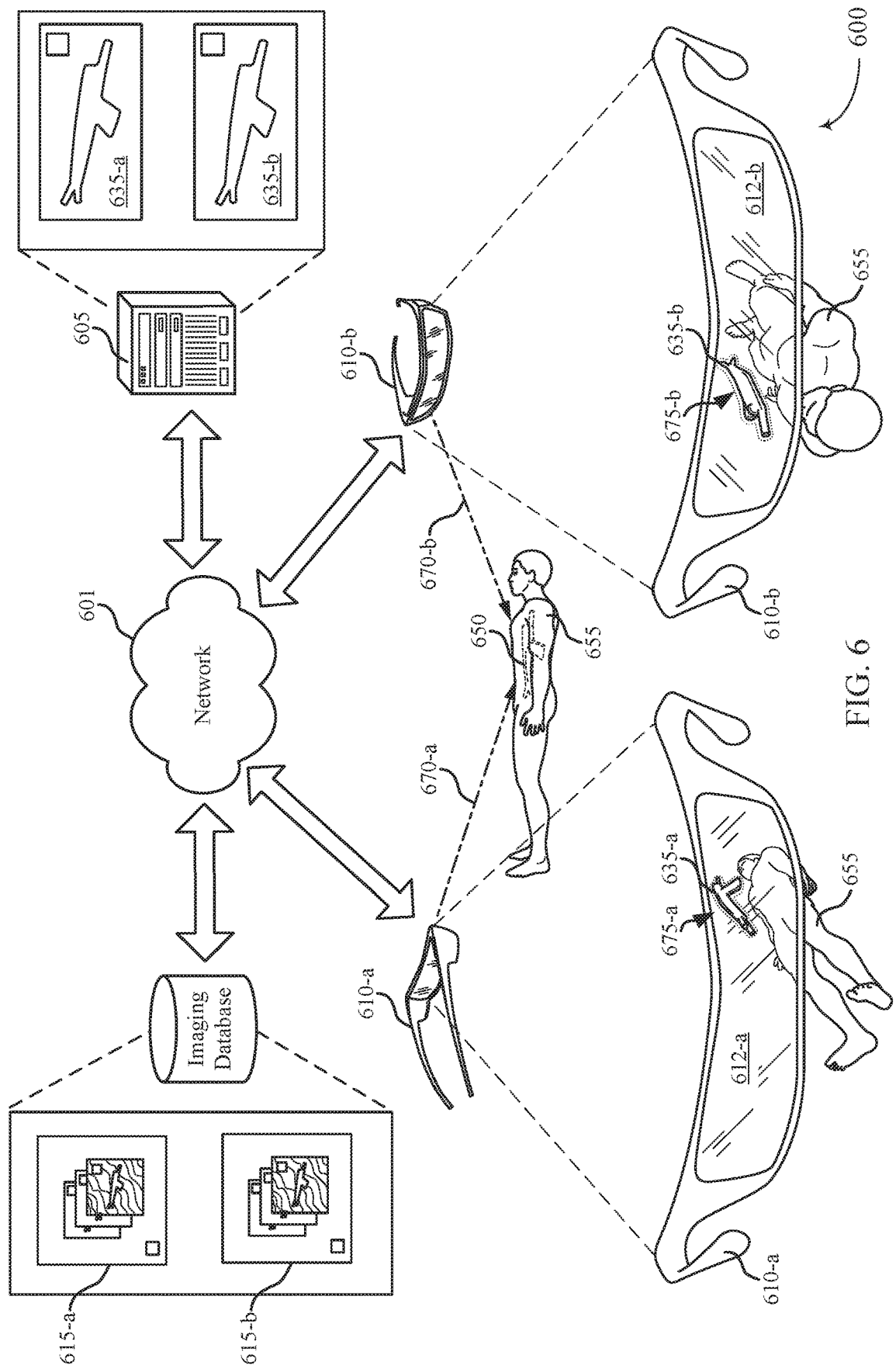
FIG. 6 illustrates an example of an AR system that supports real-time rendering and referencing for medical procedures in accordance with aspects of the present disclosure.

FIG. 6 illustrates an example of an AR system 600 that supports medical device real-time rendering and referencing system in accordance with aspects of the present disclosure. In some examples, AR system 600 may implement aspects of AR systems 100, 200, 300, 400, or 500 described in reference to FIGS. 1, 2, 3, 4, and 5. AR system 600 may include AR viewing devices 610 which may be examples of VR viewing devices 115, 210, 310, 410, or 510 described herein. AR system 600 may further include AR server 605, which may be an example of VR servers 135, 205, 305, 405, and 505 described herein, and medical imaging data 615, which may be examples of medical imaging data 155, and 215 described herein.

AR system 600 may include a first AR viewing device 610-*a* having a first view perspective 670-*a* relative to body 655 and a second AR viewing device 610-*b* having a second view perspective 670-*b* relative to body 655. In some cases, both AR viewing devices 610-*a*, 610-*b* may receive a same isolated anatomical model 635 from AR server 605. In this example, first AR viewing device 610-*a* may display isolated anatomical model 635 in first display 612-*a* at a first orientation 675-*a*. As described herein, first orientation 675-*a* may be shown on first display 612-*a* from first perspective 670-*a* based on the position of first AR viewing device 610-*a* relative to body 655. Similarly, second AR viewing device 610-*b* may display isolated anatomical model 635 on second display 612-*b* at a second orientation 675-*b*. As described herein, second orientation 675-*b* may be shown in second display 612-*b* from second perspective 670-*b* based on the position of second AR viewing device 610-*b* relative to body 655.

In some cases, first AR viewing device 610-*a* may display a first isolated anatomical model 635-*a* generated from a first set of medical imaging data 615-*a*. For example, first set of medical imaging data 615-*a* may include visual representations of biological structure 650 acquired by a first imaging modality, for example CT. In this regard, first AR viewing device 610-*a* may display first isolated anatomical model 635-*a* in first display 612-*a* where first isolated anatomical model 635-*a* is based on CT data. Additionally or alternatively, second AR viewing device 610-*b* may display a second isolated anatomical model 635-*b* generated from a second set of medical imaging data 615-*b*. For example, second set of medical imaging data 615-*b* may include visual representations of biological structure 650 acquired by a second imaging modality, for example 3D ultrasound. In this regard, second AR viewing device 610-*b* may display second isolated anatomical model 635-*b* in second display 612-*b* where second isolated anatomical model 635-*b* is based on 3D ultrasound data. Accordingly, a first user of first AR viewing device 610-*a* may view first orientation 675-*a* of first isolated anatomical model 635-*a* with CT specific data and a second user of second AR viewing device 610-*b* may view second orientation 675-*b* of second isolated anatomical model 635-*b* with ultrasound specific data. Notably, the foregoing is one illustration of how different medical imaging data 615 can be used to generate different isolated anatomical models 635 to be displayed in different AR viewing devices 610. Accordingly, various combinations of medical imaging data 615, isolated anatomical models 635, and AR viewing devices are possible.

Figure 7:
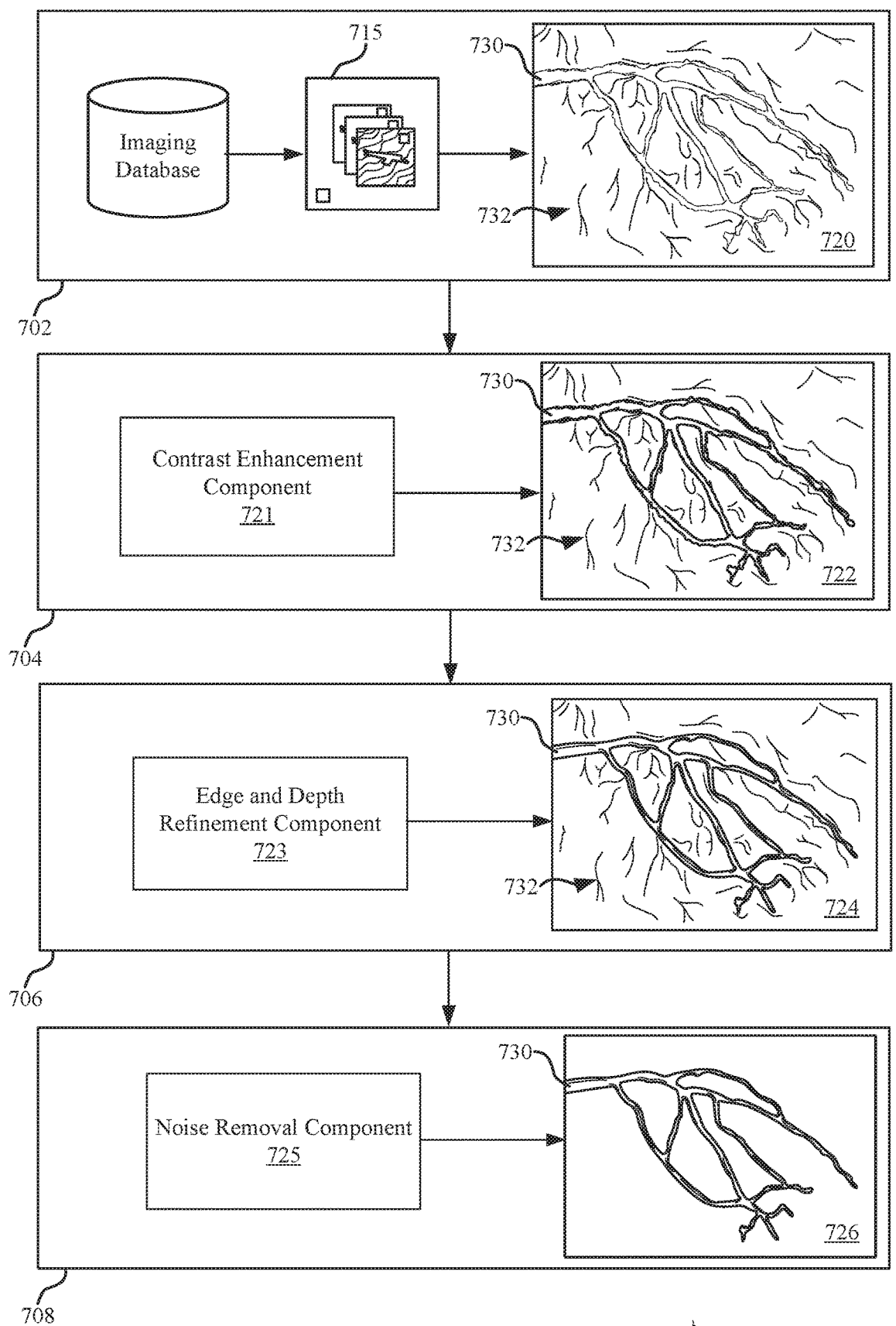
FIG. 7 illustrates an example of a rendering engine that supports real-time rendering and referencing for medical procedures in accordance with aspects of the present disclosure.

FIG. 7 illustrates an example of a rendering engine 700 that supports medical device real-time rendering and referencing system in accordance with aspects of the present disclosure. In some examples, rendering engine 700 may implement aspects of AR system 100 described in relation to FIG. 1. At 702 rendering engine 700 may receive medical imaging data 715, which may be an example of medical imaging data 155, 215, or 615 described herein. Medical imaging data 715 may include one or more medical images generated from one or more imaging modalities such as X-ray, Fluoroscopy, CT. MRI, Ultrasound, or the like. At 702, a first medical image 720 be identified for processing by rendering engine 700. First medical image 720 may include a visual representation of one or more biological structures 730. First medical image 720 may also include image noise 732, which may be other tissue, organs, or structures within a body that appear in medical image 720.

At 704, first medical image 720 may be processed by contrast enhancement component 721, to generate contrast enhanced image 722. Contrast enhancement component may darken one or more biological structures 730 and lighten image noise 732. Additionally or alternatively, contrast enhancement component 721 may sharpen edges, tissue boundaries, or other structural features of biological structure 730. At 706, contract enhanced image 722 may be processed by edge and depth refinement component 723. Edge and depth refinement component 723 may further emphasize edges, boundaries or other structural features of biological structure 730. In some cases, edge and depth refinement component 723 may rasterize or vectorize contrast enhanced image 722 to produce a refined image 724. At step 708, refined image 724 may be processed by noise removal component 725 to remove image noise 732 to isolate biological structure 730 and produce isolated biological image 726.

Rending engine 700 may perform steps 702, 704, 706 and 708 on multiple medical images such as scan data including multiple stacked scan planes of medical imaging data that are related, for example by position. In such cases, 2D or 3D models as described herein can be generated by stitching, grouping, rendering, or the like to multiple isolated biological images 726.

Figure 8:
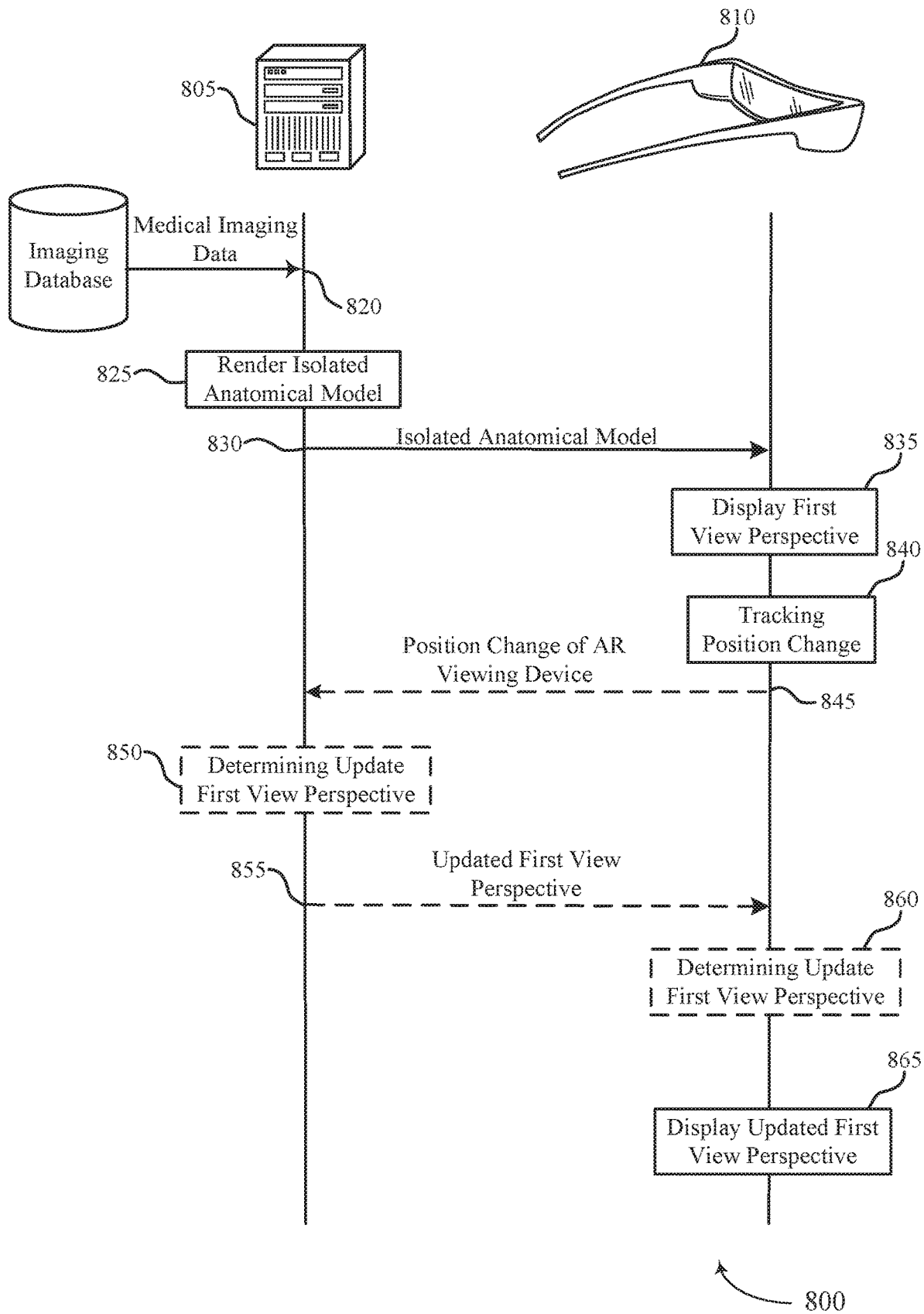
FIG. 8 illustrates an example of a process flow that supports real-time rendering and referencing for medical procedures in accordance with aspects of the present disclosure.

FIG. 8 illustrates an example of a process flow 800 that supports medical device real-time rendering and referencing system in accordance with aspects of the present disclosure. In some examples, process flow 800 may implement aspects of AR system 100, 200, 300, 400, 500, 600, or 700 as described in reference to FIGS. 1, 2, 3, 4, 5, 6, and 7. At 802, AR server 805 may receive a set of medical imaging data acquired by a first imaging modality, the set of medical imaging data comprising a visual representation of a biological structure of a body. At 825, AR server 805 may render an isolated anatomical model of at least a portion of the biological structure. At 830, AR server 805 may send the isolated anatomical model to AR viewing device 810. At 835, AR viewing device 810 may display on a display device, a first view perspective of the isolated anatomical in a first orientation based on a position of AR viewing device relative to the body. At 840, AR viewing device 810 may track a change in position of the AR viewing device 810. In some cases, at 845, AR viewing device 810 may transmit the its change in position to AR server 805. In this case, at 850 AR server may determine an updated first view perspective of isolated anatomical model based on the change in position. At 855 AR server 810 may transmit an updated first view perspective of isolated anatomical model to AR viewing device 810. Alternatively or additionally, at 860 AR viewing device 810 may determine an updated first view perspective of isolated anatomical model based on the change in position. At 865, AR viewing device 810 may display and updated first view in a second orientation based on the change in position of AR viewing device relative to the body.

Figure 9:
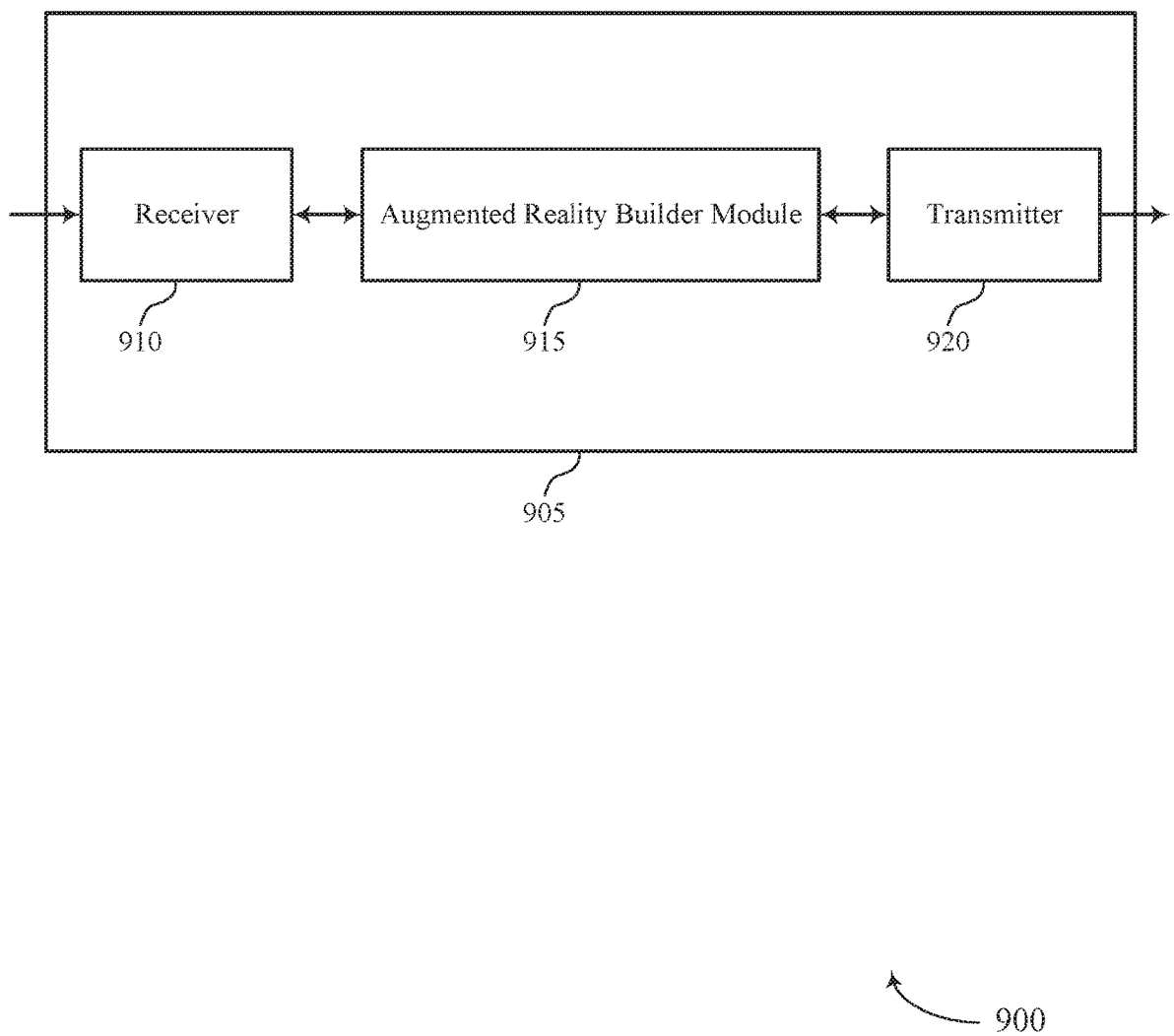
FIGS. 9 and 10 show block diagrams of devices that support real-time rendering and referencing for medical procedures in accordance with aspects of the present disclosure.

FIG. 9 shows a block diagram 900 of a device 905 that supports medical device real-time rendering and referencing system in accordance with aspects of the present disclosure. The device 905 may be an example of aspects of a device as described herein. The device 905 may include a receiver 910, an augmented reality builder module 915, and a transmitter 920. The device 905 may also include a processor. Each of these components may be in communication with one another (e.g., via one or more buses).

The receiver 910 may receive information such as packets, user data, or control information associated with various information channels (e.g., control channels, data channels, and information related to medical device real-time rendering and referencing system, etc.). Information may be passed on to other components of the device 905. The receiver 910 may be an example of aspects of the transceiver 1220 described with reference to FIG. 12. The receiver 910 may utilize a single antenna or a set of antennas.

The augmented reality builder module 915 may receive a set of imaging data acquired by at least a first imaging modality, the set of imaging data including a visual representation of a structure, render an isolated model of at least a portion of the structure, and display, on a display of an augmented reality (AR) viewing device, a first view perspective of the isolated model, where the first view perspective displays the isolated model in a first orientation based on a position of the first AR viewing device relative to viewing reference point. The augmented reality builder module 915 may be an example of aspects of the augmented reality builder module 1210 described herein.

The augmented reality builder module 915, or its sub-components, may be implemented in hardware, code (e.g., software or firmware) executed by a processor, or any combination thereof. If implemented in code executed by a processor, the functions of the augmented reality builder module 915, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The augmented reality builder module 915, or its sub-components, may be physically located at various positions, including being distributed such that portions of functions are implemented at different physical locations by one or more physical components. In some examples, the augmented reality builder module 915, or its sub-components, may be a separate and distinct component in accordance with various aspects of the present disclosure. In some examples, the augmented reality builder module 915, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

The transmitter 920 may transmit signals generated by other components of the device 905. In some examples, the transmitter 920 may be collocated with a receiver 910 in a transceiver module. For example, the transmitter 920 may be an example of aspects of the transceiver 1220 described with reference to FIG. 12. The transmitter 920 may utilize a single antenna or a set of antennas.

Figure 10:
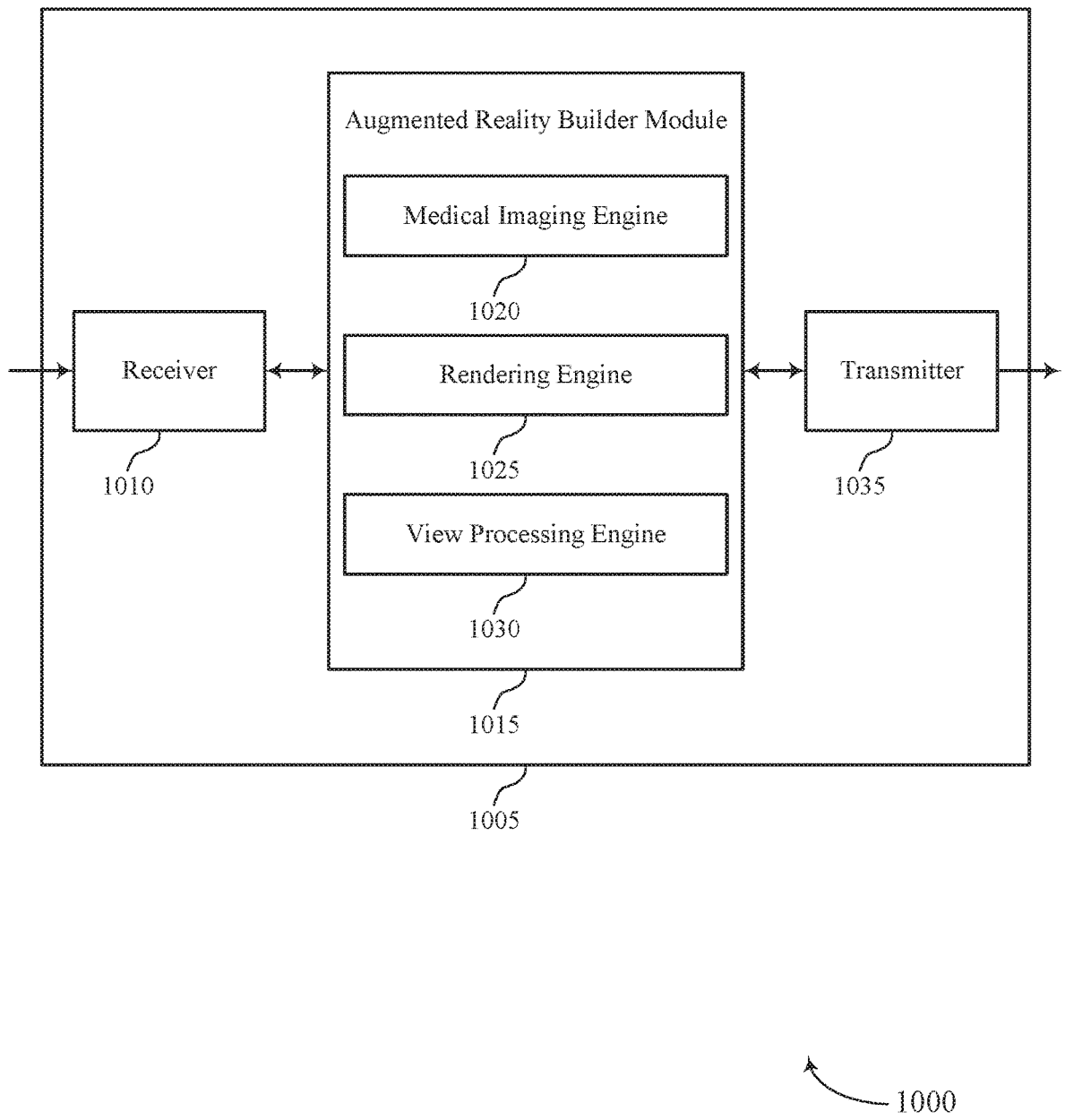

FIG. 10 shows a block diagram 1000 of a device 1005 that supports medical device real-time rendering and referencing system in accordance with aspects of the present disclosure. The device 1005 may be an example of aspects of a device 905 or a device 115 as described herein. The device 1005 may include a receiver 1010, an augmented reality builder module 1015, and a transmitter 1035. The device 1005 may also include a processor. Each of these components may be in communication with one another (e.g., via one or more buses).

The receiver 1010 may receive information such as packets, user data, or control information associated with various information channels (e.g., control channels, data channels, and information related to medical device real-time rendering and referencing system, etc.). Information may be passed on to other components of the device 1005. The receiver 1010 may be an example of aspects of the transceiver 1220 described with reference to FIG. 12. The receiver 1010 may utilize a single antenna or a set of antennas.

The augmented reality builder module 1015 may be an example of aspects of the augmented reality builder module 915 as described herein. The augmented reality builder module 1015 may include a medical imaging engine 1020, a rendering engine 1025, and a view processing engine 1030. The augmented reality builder module 1015 may be an example of aspects of the augmented reality builder module 1210 described herein.

The medical imaging engine 1020 may receive a set of imaging data acquired by at least a first imaging modality, the set of imaging data including a visual representation of a structure.

The rendering engine 1025 may render an isolated model of at least a portion of the structure.

The view processing engine 1030 may display, on a display of an augmented reality (AR) viewing device, a first view perspective of the isolated model, where the first view perspective displays the isolated model in a first orientation based on a position of the first AR viewing device relative to viewing reference point.

The transmitter 1035 may transmit signals generated by other components of the device 1005. In some examples, the transmitter 1035 may be collocated with a receiver 1010 in a transceiver module. For example, the transmitter 1035 may be an example of aspects of the transceiver 1220 described with reference to FIG. 12. The transmitter 1035 may utilize a single antenna or a set of antennas.

Figure 11:
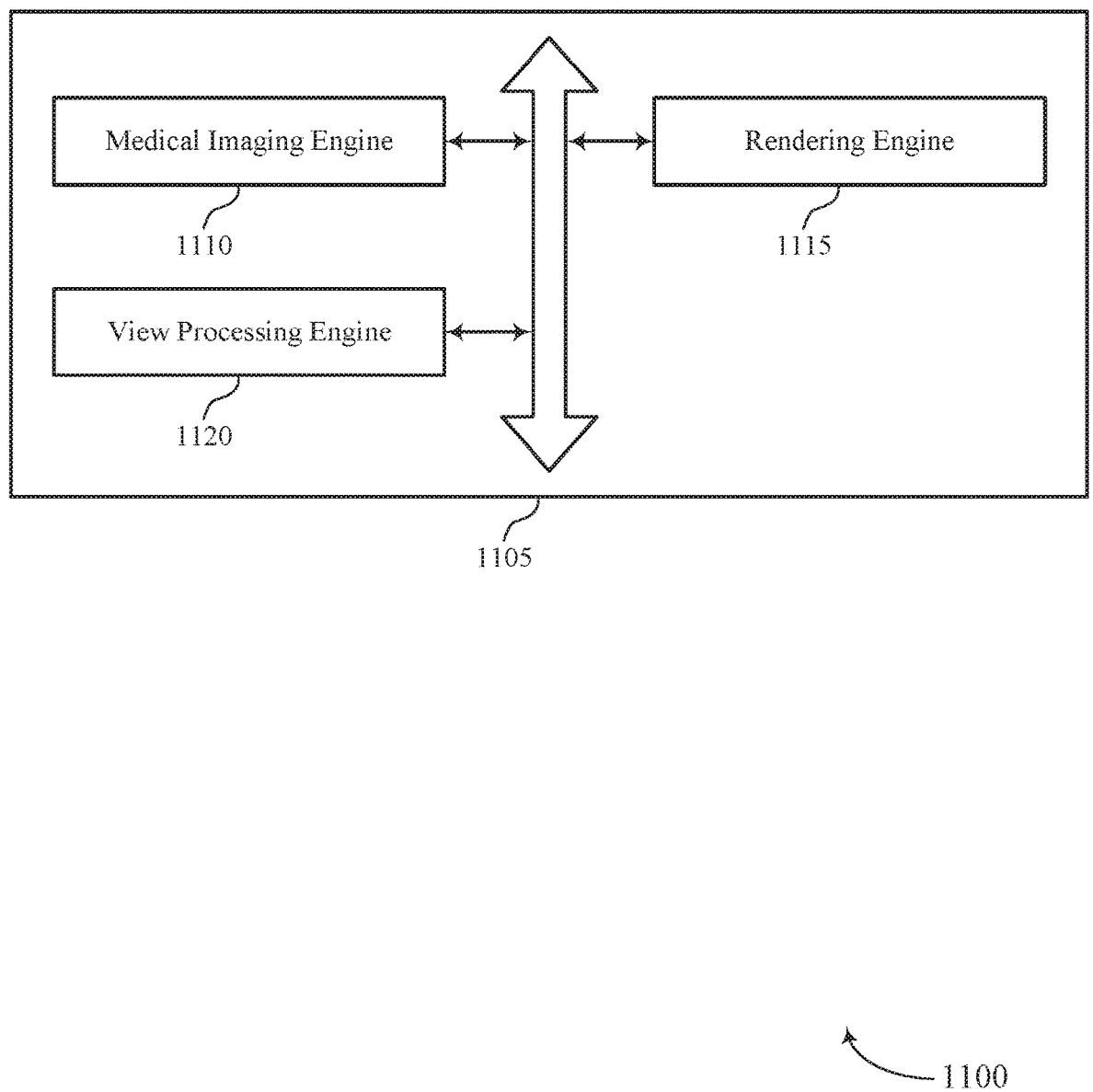
FIG. 11 shows a block diagram of an augmented reality builder module that supports real-time rendering and referencing for medical procedures in accordance with aspects of the present disclosure.

FIG. 11 shows a block diagram 1100 of an augmented reality builder module 1105 that supports medical device real-time rendering and referencing system in accordance with aspects of the present disclosure. The augmented reality builder module 1105 may be an example of aspects of a augmented reality builder module 915, an augmented reality builder module 1015, or an augmented reality builder module 1210 described herein. The augmented reality builder module 1105 may include a medical imaging engine 1110, a rendering engine 1115, and a view processing engine 1120. Each of these modules may communicate, directly or indirectly, with one another (e.g., via one or more buses).

The medical imaging engine 1110 may receive a set of imaging data acquired by at least a first imaging modality, the set of imaging data including a visual representation of a structure.

In some cases, the structure includes at least a set of internal features that are contained within the interior of the structure.

In some cases, the set of imaging data includes a visual representation of at least a portion of the set of internal features.

The rendering engine 1115 may render an isolated model of at least a portion of the structure.

The view processing engine 1120 may display, on a display of an augmented reality (AR) viewing device, a first view perspective of the isolated model, where the first view perspective displays the isolated model in a first orientation based on a position of the first AR viewing device relative to viewing reference point.

Figure 12:
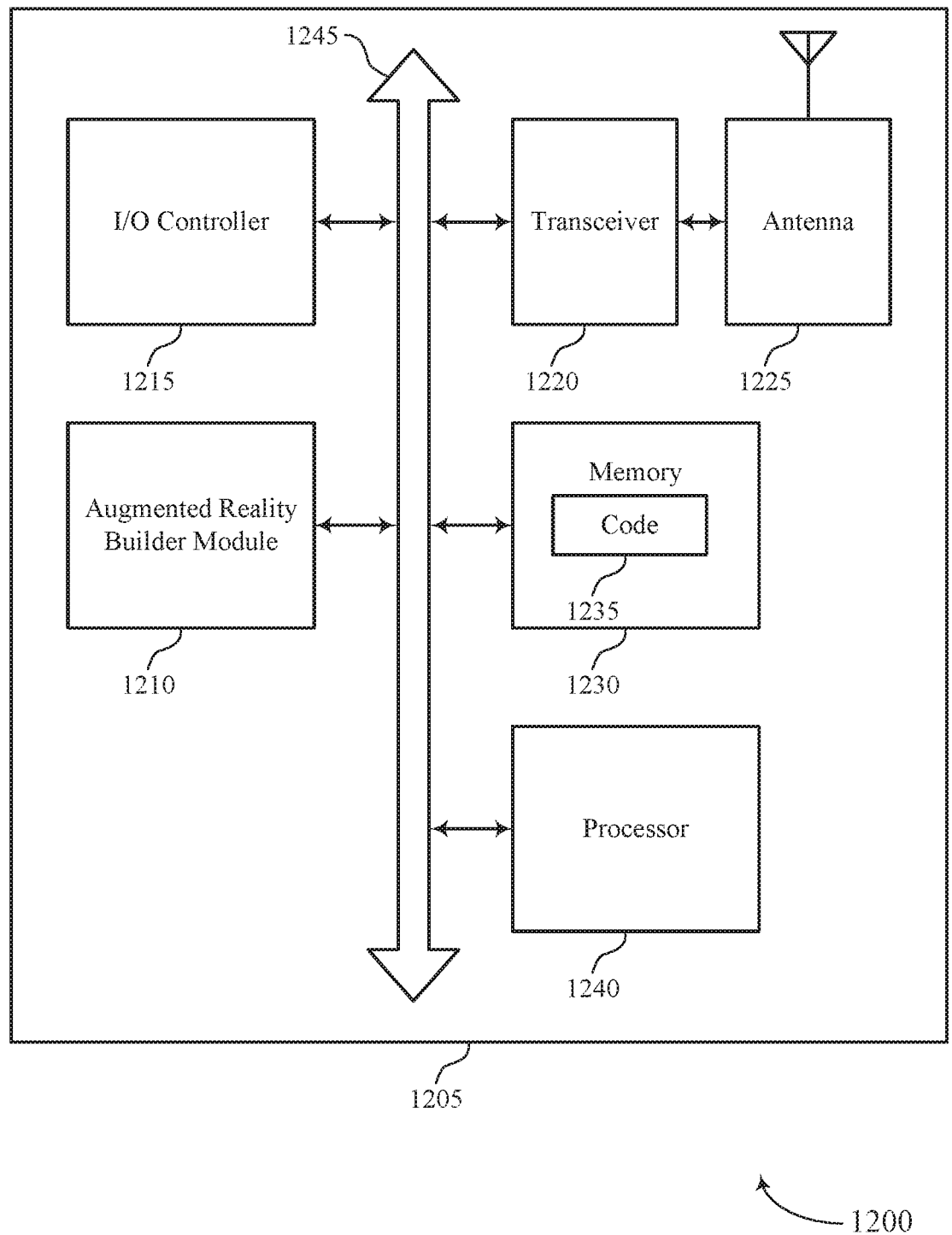
FIG. 12 shows a diagram of a system including a device that supports real-time rendering and referencing for medical procedures in accordance with aspects of the present disclosure.

FIG. 12 shows a diagram of a system 1200 including a device 1205 that supports medical device real-time rendering and referencing system in accordance with aspects of the present disclosure. The device 1205 may be an example of or include the components of device 905, device 1005, or a device as described herein. The device 1205 may include components for bi-directional voice and data communications including components for transmitting and receiving communications, including an augmented reality builder module 1210, an I/O controller 1215, a transceiver 1220, an antenna 1225, memory 1230, and a processor 1240. These components may be in electronic communication via one or more buses (e.g., bus 1245).

The augmented reality builder module 1210 may receive a set of imaging data acquired by at least a first imaging modality, the set of imaging data including a visual representation of a structure, render an isolated model of at least a portion of the structure, and display, on a display of an augmented reality (AR) viewing device, a first view perspective of the isolated model, where the first view perspective displays the isolated model in a first orientation based on a position of the first AR viewing device relative to viewing reference point.

The I/O controller 1215 may manage input and output signals for the device 1205. The I/O controller 1215 may also manage peripherals not integrated into the device 1205. In some cases, the I/O controller 1215 may represent a physical connection or port to an external peripheral. In some cases, the I/O controller 1215 may utilize an operating system such as iOS®, ANDROID®, MS-DOS®, MS-WINDOWS®, OS/2®, UNIX®, LINUX®, or another known operating system. In other cases, the I/O controller 1215 may represent or interact with a modem, a keyboard, a mouse, a touchscreen, or a similar device. In some cases, the I/O controller 1215 may be implemented as part of a processor. In some cases, a user may interact with the device 1205 via the I/O controller 1215 or via hardware components controlled by the I/O controller 1215.

The transceiver 1220 may communicate bi-directionally, via one or more antennas, wired, or wireless links as described above. For example, the transceiver 1220 may represent a wireless transceiver and may communicate bi-directionally with another wireless transceiver. The transceiver 1220 may also include a modem to modulate the packets and provide the modulated packets to the antennas for transmission, and to demodulate packets received from the antennas.

In some cases, the wireless device may include a single antenna 1225. However, in some cases the device may have more than one antenna 1225, which may be capable of concurrently transmitting or receiving multiple wireless transmissions.

The memory 1230 may include RAM and ROM. The memory 1230 may store computer-readable, computer-executable code 1235 including instructions that, when executed, cause the processor to perform various functions described herein. In some cases, the memory 1230 may contain, among other things, a BIOS which may control basic hardware or software operation such as the interaction with peripheral components or devices.

The processor 1240 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1240 may be configured to operate a memory array using a memory controller. In other cases, a memory controller may be integrated into the processor 1240. The processor 1240 may be configured to execute computer-readable instructions stored in a memory (e.g., the memory 1230) to cause the device 1205 to perform various functions (e.g., functions or tasks supporting medical device real-time rendering and referencing system).

The code 1235 may include instructions to implement aspects of the present disclosure, including instructions to support medical imaging. The code 1235 may be stored in a non-transitory computer-readable medium such as system memory or other type of memory. In some cases, the code 1235 may not be directly executable by the processor 1240 but may cause a computer (e.g., when compiled and executed) to perform functions described herein.

Figure 13:
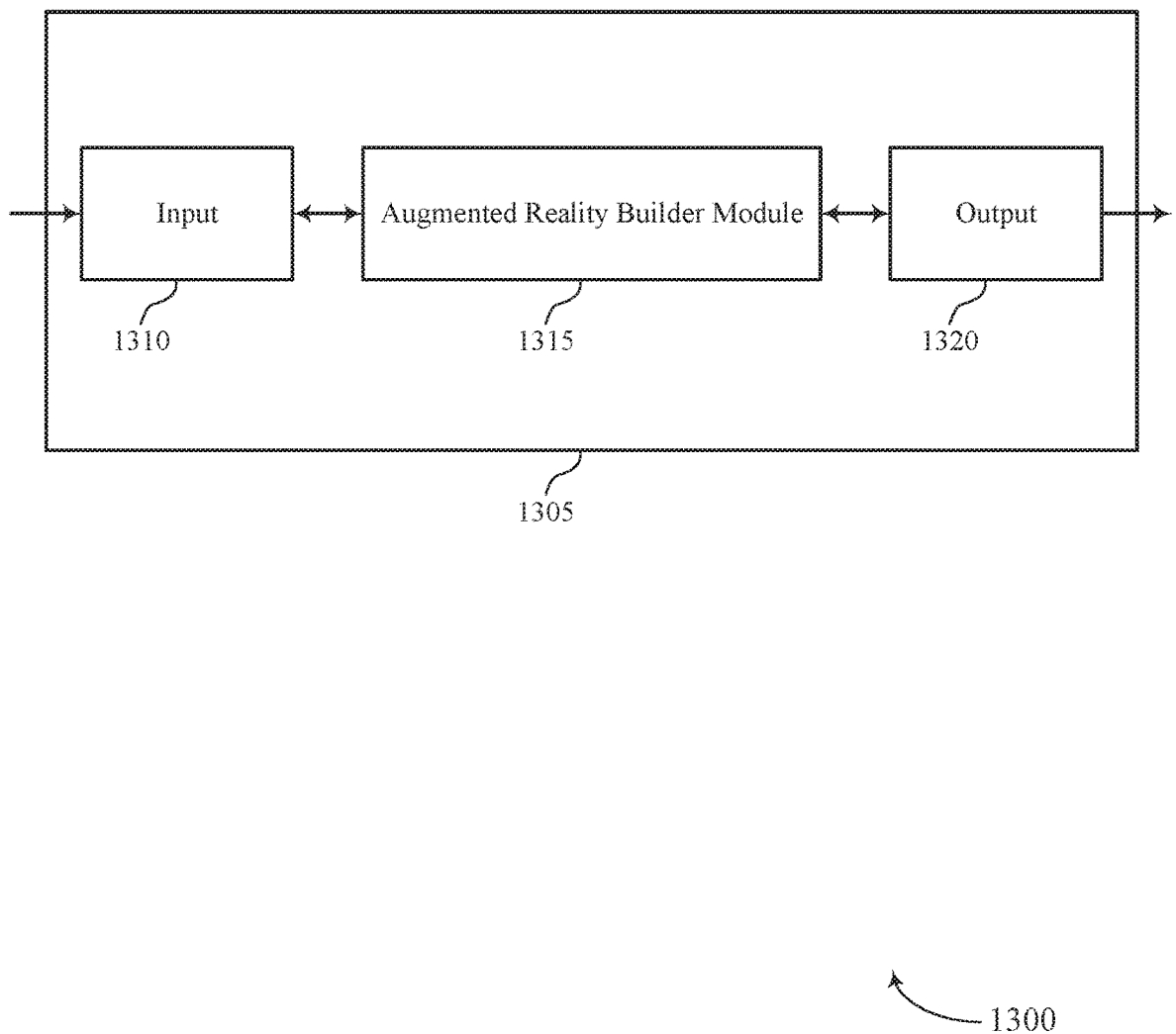
FIGS. 13 and 14 show block diagrams of devices that support real-time rendering and referencing for medical procedures in accordance with aspects of the present disclosure.

FIG. 13 shows a block diagram 1300 of a device 1305 that supports medical device real-time rendering and referencing system in accordance with aspects of the present disclosure. The device 1305 may be an example of aspects of a medical data server as described herein. The device 1305 may include an input 1310, an augmented reality builder module 1315, and an output 1320. The device 1305 may also include a processor. Each of these components may be in communication with one another (e.g., via one or more buses).

Undefined

The augmented reality builder module 1315 may receive a set of medical imaging data acquired by at least a first imaging modality, the set of medical imaging data including a visual representation of a biological structure of a body, render an isolated anatomical model of at least a portion of the biological structure, and display, on a display of an augmented reality (AR) viewing device, a first view perspective of the isolated anatomical model, where the first view perspective displays the isolated anatomical model in a first orientation based on a position of the first AR viewing device relative to the body. The augmented reality builder module 1315 may also display, in a display device of an augmented reality (AR) viewing device, a first view perspective of an isolated anatomical model in a first orientation based on a position of the first AR viewing device relative to the body, receive position data of a medical instrument relative to a reference point of the body, where the medical instrument is located within an interior of the body, and display a virtual position of the medical instrument in the first view perspective of the AR view device, where the virtual position of the medical instrument is displayed at a relative position to the isolated anatomical model based at least on part on the received position data of the medical instrument. The augmented reality builder module 1315 may be an example of aspects of the augmented reality builder module 1610 described herein.

The augmented reality builder module 1315, or its sub-components, may be implemented in hardware, code (e.g., software or firmware) executed by a processor, or any combination thereof. If implemented in code executed by a processor, the functions of the augmented reality builder module 1315, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The augmented reality builder module 1315, or its sub-components, may be physically located at various positions, including being distributed such that portions of functions are implemented at different physical locations by one or more physical components. In some examples, the augmented reality builder module 1315, or its sub-components, may be a separate and distinct component in accordance with various aspects of the present disclosure. In some examples, the augmented reality builder module 1315, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

Undefined

Figure 14:
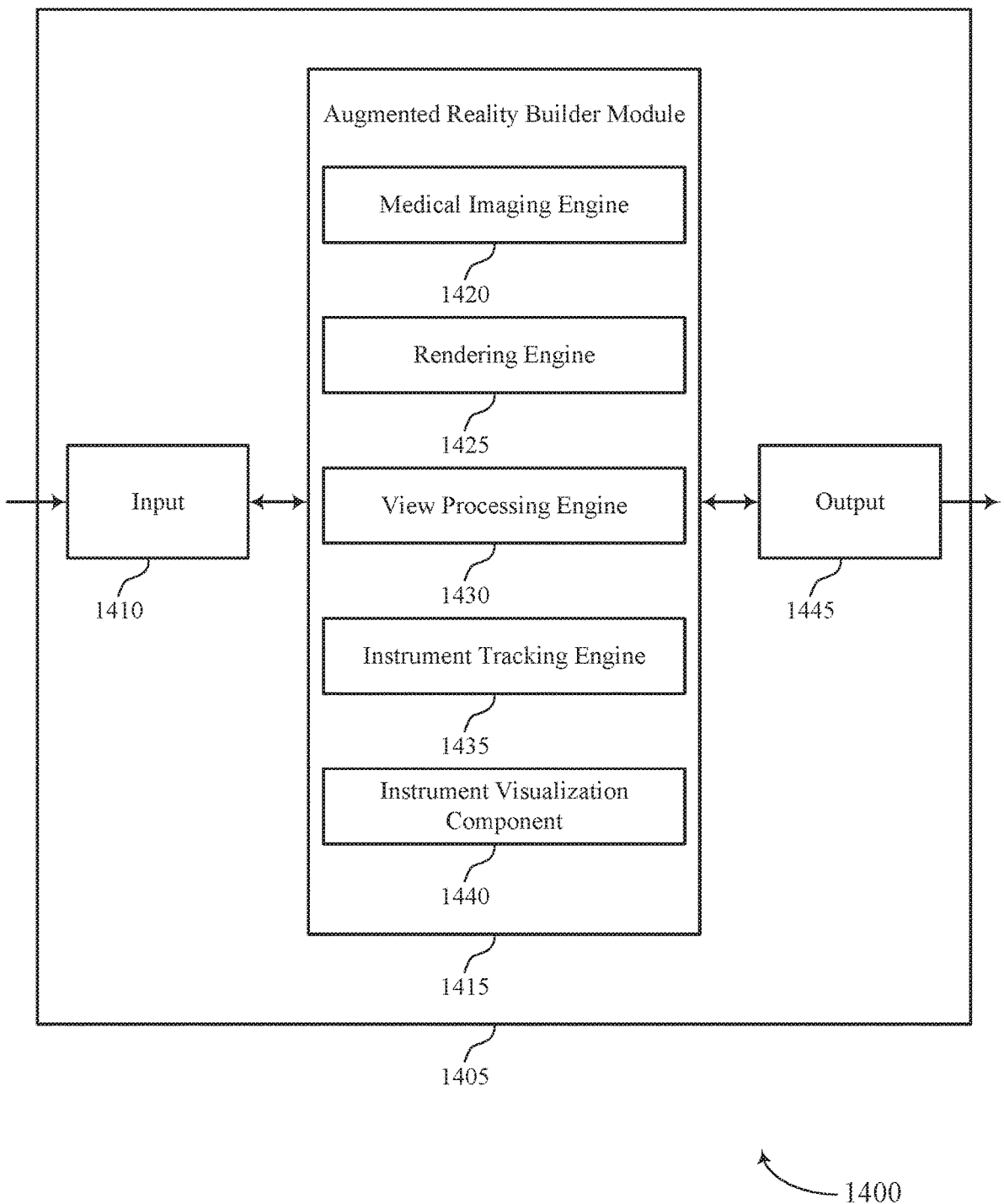

FIG. 14 shows a block diagram 1400 of a device 1405 that supports medical device real-time rendering and referencing system in accordance with aspects of the present disclosure. The device 1405 may be an example of aspects of a device 1305 or a medical data server 115 as described herein. The device 1405 may include an input 1410, an augmented reality builder module 1415, and an output 1445. The device 1405 may also include a processor. Each of these components may be in communication with one another (e.g., via one or more buses).

Undefined

The augmented reality builder module 1415 may be an example of aspects of the augmented reality builder module 1315 as described herein. The augmented reality builder module 1415 may include a medical imaging engine 1420, a rendering engine 1425, a view processing engine 1430, an instrument tracking engine 1435, and an instrument visualization component 1440. The augmented reality builder module 1415 may be an example of aspects of the augmented reality builder module 1610 described herein.

The medical imaging engine 1420 may receive a set of medical imaging data acquired by at least a first imaging modality, the set of medical imaging data including a visual representation of a biological structure of a body.

The rendering engine 1425 may render an isolated anatomical model of at least a portion of the biological structure.

The view processing engine 1430 may display, on a display of an augmented reality (AR) viewing device, a first view perspective of the isolated anatomical model, where the first view perspective displays the isolated anatomical model in a first orientation based on a position of the first AR viewing device relative to the body.

The view processing engine 1430 may display, in a display device of an augmented reality (AR) viewing device, a first view perspective of an isolated anatomical model in a first orientation based on a position of the first AR viewing device relative to the body.

The instrument tracking engine 1435 may receive position data of a medical instrument relative to a reference point of the body, where the medical instrument is located within an interior of the body.

The instrument visualization component 1440 may display a virtual position of the medical instrument in the first view perspective of the AR view device, where the virtual position of the medical instrument is displayed at a relative position to the isolated anatomical model based at least on part on the received position data of the medical instrument.

Figure 15:
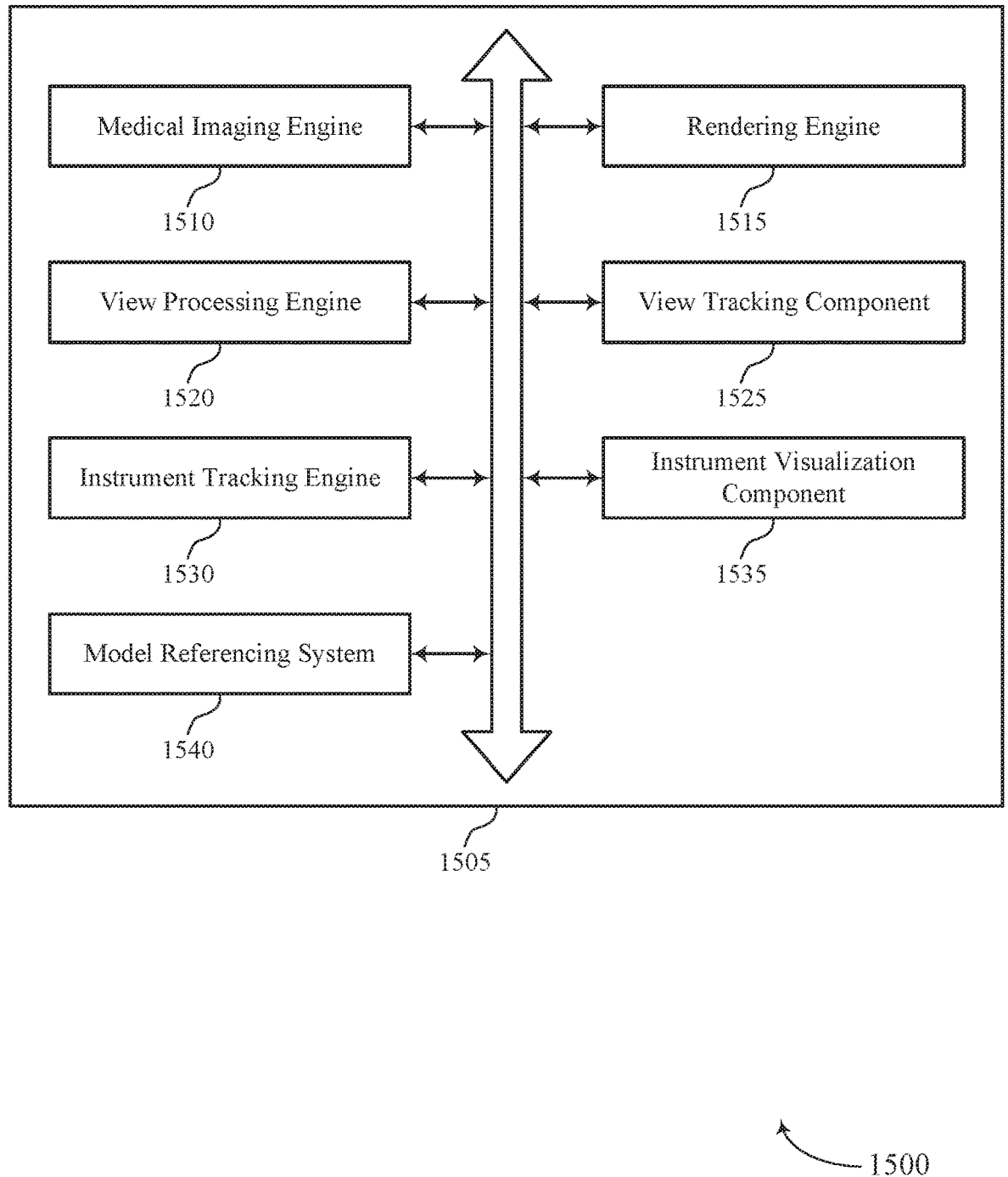
FIG. 15 shows a block diagram of an augmented reality builder module that supports real-time rendering and referencing for medical procedures in accordance with aspects of the present disclosure.

FIG. 15 shows a block diagram 1500 of an augmented reality builder module 1505 that supports medical device real-time rendering and referencing system in accordance with aspects of the present disclosure. The augmented reality builder module 1505 may be an example of aspects of an augmented reality builder module 1315, an augmented reality builder module 1415, or an augmented reality builder module 1610 described herein. The augmented reality builder module 1505 may include a medical imaging engine 1510, a rendering engine 1515, a view processing engine 1520, a view tracking component 1525, an instrument tracking engine 1530, an instrument visualization component 1535, and a model referencing system 1540. Each of these modules may communicate, directly or indirectly, with one another (e.g., via one or more buses).

The medical imaging engine 1510 may receive a set of medical imaging data acquired by at least a first imaging modality, the set of medical imaging data including a visual representation of a biological structure of a body.

The rendering engine 1515 may render an isolated anatomical model of at least a portion of the biological structure.

The view processing engine 1520 may display, on a display of an augmented reality (AR) viewing device, a first view perspective of the isolated anatomical model, where the first view perspective displays the isolated anatomical model in a first orientation based on a position of the first AR viewing device relative to the body.

In some examples, the view processing engine 1520 may display, in a display device of an augmented reality (AR) viewing device, a first view perspective of an isolated anatomical model in a first orientation based on a position of the first AR viewing device relative to the body.

In some examples, the view processing engine 1520 may display a real-time position of the first view perspective of the isolated anatomical model based on tracking the real-time change in position of the AR viewing device.

In some examples, updating the first view perspective of the isolated anatomical model based on a change in position of the AR viewing device relative to the body, where updating the first view perspective includes displaying the isolated anatomical model in a second orientation based on the change in position of the AR viewing device.

In some examples, the view processing engine 1520 may display an anchoring position of the isolated anatomical model within the first view perspective of the AR viewing device, where the anchoring position orients the isolated anatomical model to align with the medical imaging reference orientation.

In some examples, updating the first view perspective of the isolated anatomical model in response to a change in position of the AR viewing device, where the updating includes maintaining the isolated anatomical model in the anchoring position relative to the body.

In some examples, the view processing engine 1520 may receive a command to change the orientation of the isolated anatomical model from the anchoring position to a selected position.

In some examples, the view processing engine 1520 may display, on the display the AR viewing device, a second view perspective of the isolated anatomical model, where the second view perspective of the isolated anatomical model displays the isolated anatomical model at the selected position based on the position of the AR viewing device relative to the body.

In some examples, the view processing engine 1520 may display, on a display of a second AR viewing device, a third view perspective of the isolated anatomical model, where the third view perspective displays the isolated anatomical model in a third orientation based on a position of the second AR viewing device relative to the body.

In some cases, the anchoring position orients the isolated anatomical model in the first view perspective of the AR viewing device to appear at a location above the body.

The instrument tracking engine 1530 may receive position data of a medical instrument relative to a reference point of the body, where the medical instrument is located within an interior of the body.

In some examples, the instrument tracking engine 1530 may receive real-time position data of a medical instrument relative to a reference point of the body.

In some examples, the instrument tracking engine 1530 may compute a virtual position of a representation of the medical instrument relative to the isolated anatomical model based on the received real-time position data of the medical instrument.

In some examples, the instrument tracking engine 1530 may receive signal data from an active tracking component located on the medical instrument.

In some examples, the instrument tracking engine 1530 may receive at least a portion of the real-time position data of the medical instrument from a navigation instrument located outside the body.

In some cases, the computing the virtual position of the representation of the medical instrument corresponds to a real-time position of the medical instrument relative to the reference point of the body.

In some cases, the signal data includes at least one of a force measurement, an ultrasonic measurement, a magnetic measurement, an orientation measurement, or a combination thereof.

In some cases, the real-time position data of the medical instrument includes at least one of ultrasonic data, radio frequency identification (RFID) sensor data, contrast imaging data, GPS data, orientation data, or a combination thereof.

The instrument visualization component 1535 may display a virtual position of the medical instrument in the first view perspective of the AR view device, where the virtual position of the medical instrument is displayed at a relative position to the isolated anatomical model based at least on part on the received position data of the medical instrument.

In some examples, the instrument visualization component 1535 may display a real-time virtual position of the medical instrument in the first view perspective of the AR viewing device, where the real-time virtual position of the medical instrument is oriented within the isolated anatomical model based on the received real-time position data of the medical instrument relative to the reference point of the body.

The view tracking component 1525 may track a real-time change in position of the AR viewing device.

The model referencing system 1540 may determine a medical imaging reference orientation based on receiving the set of medical imaging data, where the medical imaging reference orientation includes position data of the visual representation of the biological structure relative to the body.

Figure 16:
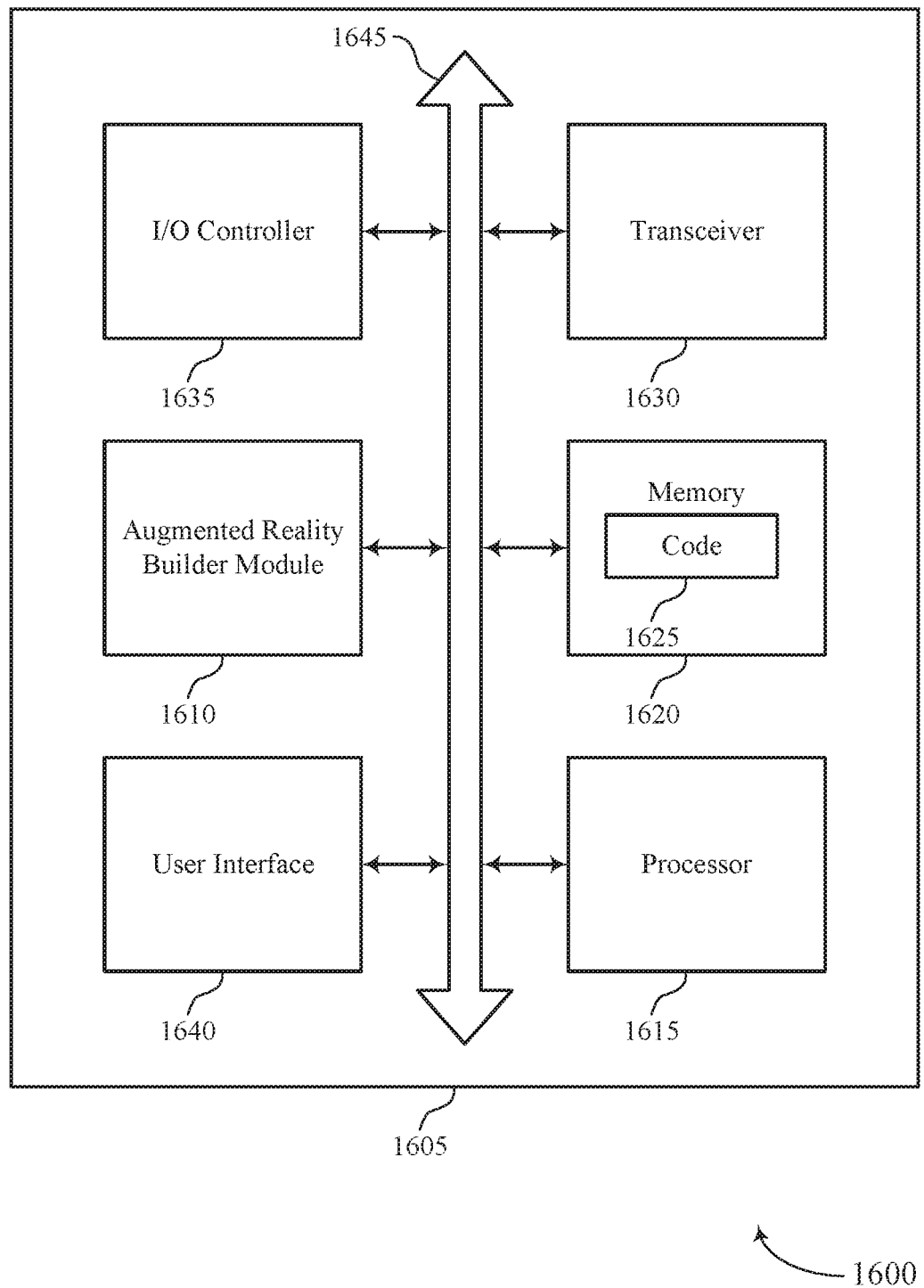
FIG. 16 shows a diagram of a system including a device that supports real-time rendering and referencing for medical procedures in accordance with aspects of the present disclosure.

FIG. 16 shows a diagram of a system 1600 including a device 1605 that supports medical device real-time rendering and referencing system in accordance with aspects of the present disclosure. The device 1605 may be an example of or include the components of device 1305, device 1405, or a medical data server as described herein. The device 1605 may include components for bi-directional voice and data communications including components for transmitting and receiving communications, including an augmented reality builder module 1610, a processor 1615, memory 1620, a transceiver 1630, an I/O controller 1635, and a user interface 1640. These components may be in electronic communication via one or more buses (e.g., bus 1645).

The augmented reality builder module 1610 may receive a set of medical imaging data acquired by at least a first imaging modality, the set of medical imaging data including a visual representation of a biological structure of a body, render an isolated anatomical model of at least a portion of the biological structure, and display, on a display of an augmented reality (AR) viewing device, a first view perspective of the isolated anatomical model, where the first view perspective displays the isolated anatomical model in a first orientation based on a position of the first AR viewing device relative to the body. The augmented reality builder module 1610 may also display, in a display device of an augmented reality (AR) viewing device, a first view perspective of an isolated anatomical model in a first orientation based on a position of the first AR viewing device relative to the body, receive position data of a medical instrument relative to a reference point of the body, where the medical instrument is located within an interior of the body, and display a virtual position of the medical instrument in the first view perspective of the AR view device, where the virtual position of the medical instrument is displayed at a relative position to the isolated anatomical model based at least on part on the received position data of the medical instrument.

Processor 1615 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, processor 1615 may be configured to operate a memory array using a memory controller. In other cases, a memory controller may be integrated into processor 1615. Processor 1615 may be configured to execute computer-readable instructions stored in a memory to perform various functions (e.g., functions or tasks supporting medical device real-time rendering and referencing system).

Memory 1620 may include RAM and ROM. The memory 1620 may store computer-readable, computer-executable software 1625 including instructions that, when executed, cause the processor to perform various functions described herein. In some cases, the memory 1620 may contain, among other things, a BIOS which may control basic hardware or software operation such as the interaction with peripheral components or devices.

Software 1625 may include code to implement aspects of the present disclosure, including code to support video conferencing and virtual appointments. Software 1625 may be stored in a non-transitory computer-readable medium such as system memory or other memory. In some cases, the software 1625 may not be directly executable by the processor but may cause a computer (e.g., when compiled and executed) to perform functions described herein.

Transceiver 1630 may communicate bi-directionally, via one or more antennas, wired, or wireless links as described above. For example, the transceiver 1630 may represent a wireless transceiver and may communicate bi-directionally with another wireless transceiver. The transceiver 1630 may also include a modem to modulate the packets and provide the modulated packets to the antennas for transmission, and to demodulate packets received from the antennas.

I/O controller 1635 may manage input and output signals for device 1605. I/O controller 1635 may also manage peripherals not integrated into device 1605. In some cases, I/O controller 1635 may represent a physical connection or port to an external peripheral. In some cases, I/O controller 1635 may utilize an operating system such as iOS®, ANDROID®, MS-DOS®, MS-WINDOWS®, OS/2®, UNIX®, LINUX®, or another known operating system. In other cases, I/O controller 1635 may represent or interact with a modem, a keyboard, a mouse, a touchscreen, or a similar device. In some cases, I/O controller 1635 may be implemented as part of a processor. In some cases, a user may interact with device 1605 via I/O controller 1635 or via hardware components controlled by I/O controller 1635.

User interface 1640 may enable a user to interact with device 1605. In some embodiments, the user interface module 1640 may include an audio device, such as an external speaker system, an external display device such as a display screen, or an input device (e.g., remote control device interfaced with the user interface module 1640 directly or through the I/O controller module).

Figure 17:
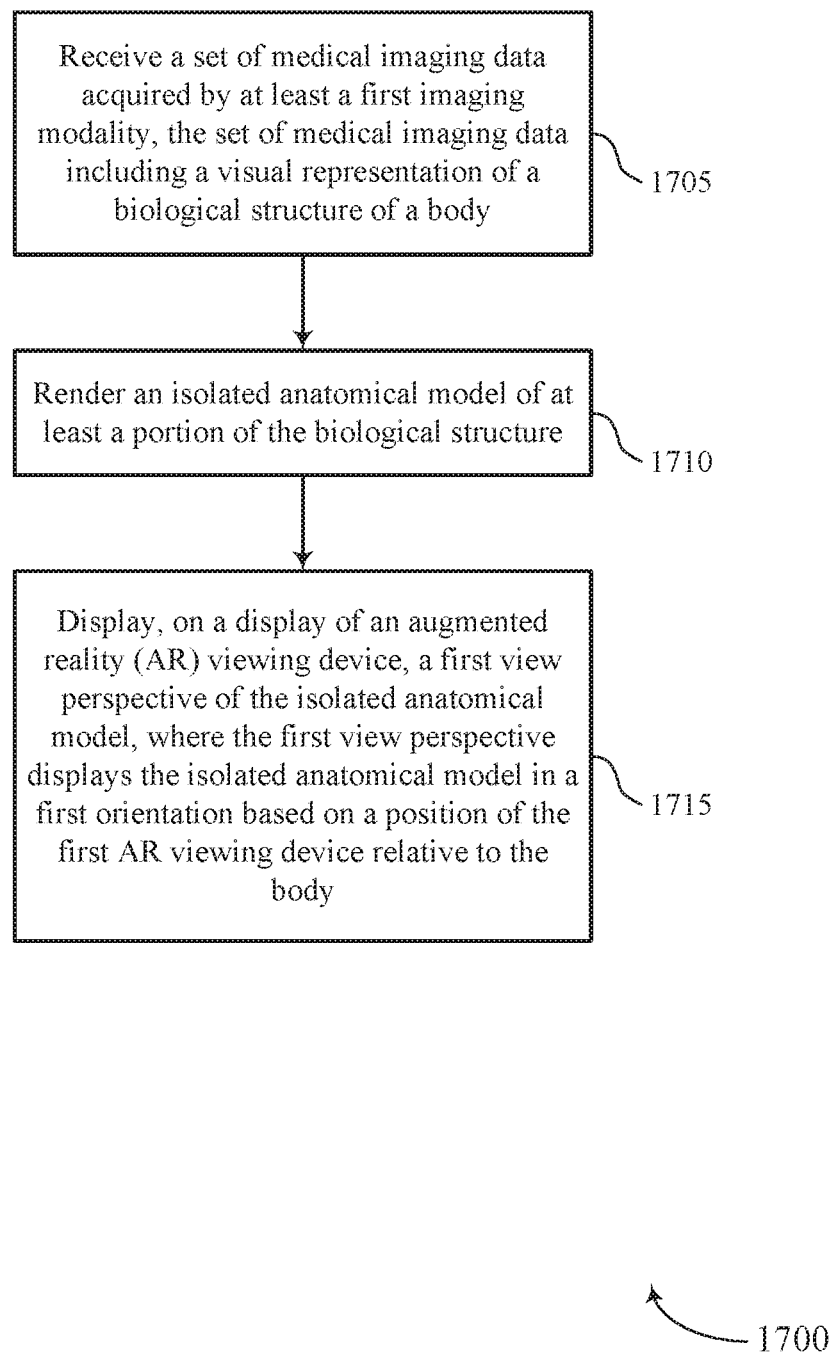
FIGS. 17 through 21 show flowcharts illustrating methods that support real-time rendering and referencing for medical procedures in accordance with aspects of the present disclosure.

FIG. 17 shows a flowchart illustrating a method 1700 that supports medical device real-time rendering and referencing system in accordance with aspects of the present disclosure. The operations of method 1700 may be implemented by a medical data server or its components as described herein. For example, the operations of method 1700 may be performed by an augmented reality builder module as described with reference to FIGS. 13 through 16. In some examples, a medical data server may execute a set of instructions to control the functional elements of the medical data server to perform the functions described below. Additionally or alternatively, a medical data server may perform aspects of the functions described below using special-purpose hardware.

At 1705, the medical data server may receive a set of medical imaging data acquired by at least a first imaging modality, the set of medical imaging data including a visual representation of a biological structure of a body. The operations of 1705 may be performed according to the methods described herein. In some examples, aspects of the operations of 1705 may be performed by a medical imaging engine as described with reference to FIGS. 13 through 16.

At 1710, the medical data server may render an isolated anatomical model of at least a portion of the biological structure. The operations of 1710 may be performed according to the methods described herein. In some examples, aspects of the operations of 1710 may be performed by a rendering engine as described with reference to FIGS. 13 through 16.

At 1715, the medical data server may display, on a display of an augmented reality (AR) viewing device, a first view perspective of the isolated anatomical model, where the first view perspective displays the isolated anatomical model in a first orientation based on a position of the first AR viewing device relative to the body. The operations of 1715 may be performed according to the methods described herein. In some examples, aspects of the operations of 1715 may be performed by a view processing engine as described with reference to FIGS. 13 through 16.

Figure 18:
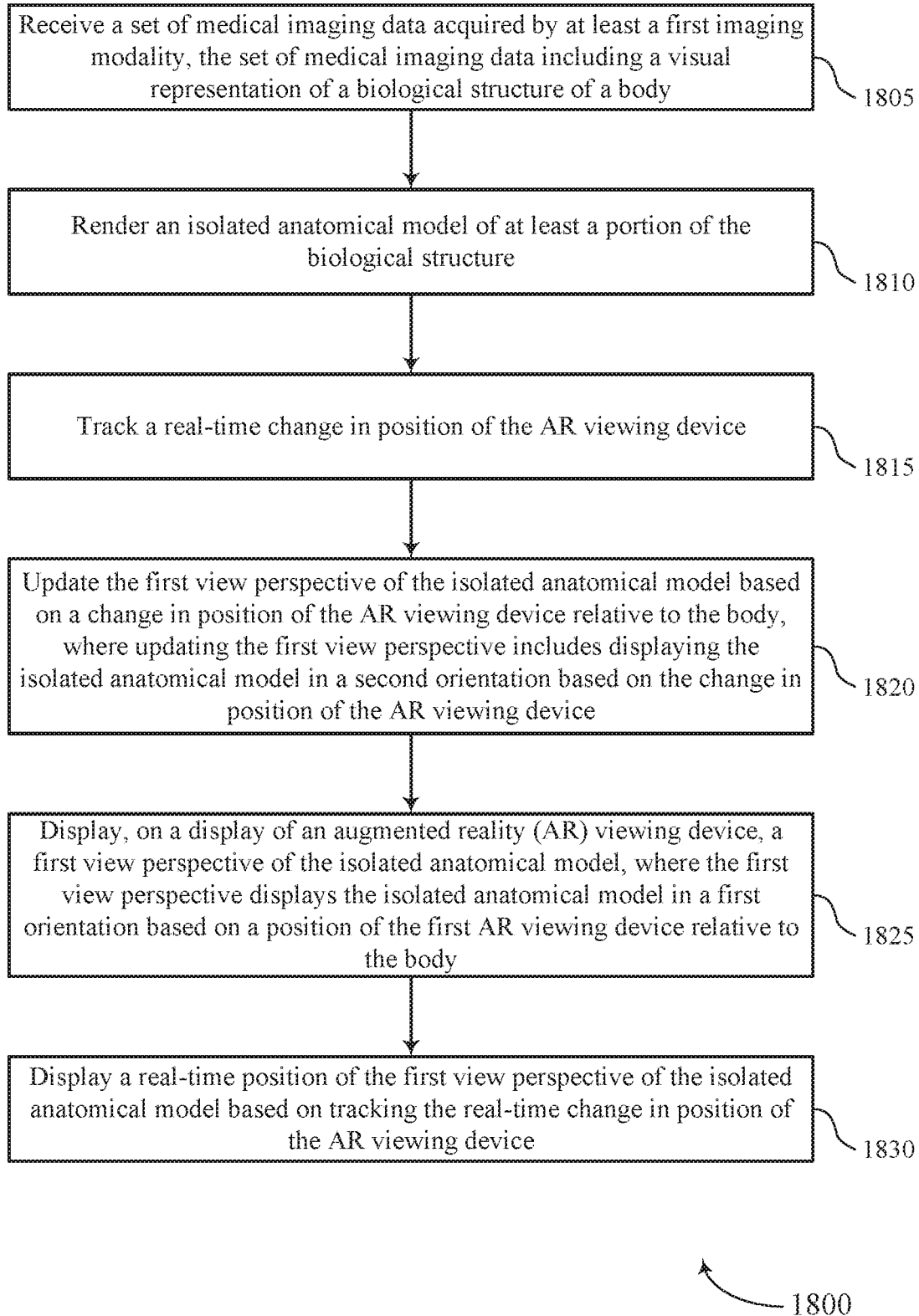

FIG. 18 shows a flowchart illustrating a method 1800 that supports medical device real-time rendering and referencing system in accordance with aspects of the present disclosure. The operations of method 1800 may be implemented by a medical data server or its components as described herein. For example, the operations of method 1800 may be performed by an augmented reality builder module as described with reference to FIGS. 13 through 16. In some examples, a medical data server may execute a set of instructions to control the functional elements of the medical data server to perform the functions described below. Additionally or alternatively, a medical data server may perform aspects of the functions described below using special-purpose hardware.

At 1805, the medical data server may receive a set of medical imaging data acquired by at least a first imaging modality, the set of medical imaging data including a visual representation of a biological structure of a body. The operations of 1805 may be performed according to the methods described herein. In some examples, aspects of the operations of 1805 may be performed by a medical imaging engine as described with reference to FIGS. 13 through 16.

At 1810, the medical data server may render an isolated anatomical model of at least a portion of the biological structure. The operations of 1810 may be performed according to the methods described herein. In some examples, aspects of the operations of 1810 may be performed by a rendering engine as described with reference to FIGS. 13 through 16.

At 1815, the medical data server may track a real-time change in position of the AR viewing device. The operations of 1815 may be performed according to the methods described herein. In some examples, aspects of the operations of 1815 may be performed by a view tracking component as described with reference to FIGS. 13 through 16.

At 1820, the medical data server may update the first view perspective of the isolated anatomical model based on a change in position of the AR viewing device relative to the body, where updating the first view perspective includes displaying the isolated anatomical model in a second orientation based on the change in position of the AR viewing device. The operations of 1820 may be performed according to the methods described herein. In some examples, aspects of the operations of 1820 may be performed by a view processing engine as described with reference to FIGS. 13 through 16.

At 1825, the medical data server may display, on a display of an augmented reality (AR) viewing device, a first view perspective of the isolated anatomical model, where the first view perspective displays the isolated anatomical model in a first orientation based on a position of the first AR viewing device relative to the body. The operations of 1825 may be performed according to the methods described herein. In some examples, aspects of the operations of 1825 may be performed by a view processing engine as described with reference to FIGS. 13 through 16.

At 1830, the medical data server may display a real-time position of the first view perspective of the isolated anatomical model based on tracking the real-time change in position of the AR viewing device. The operations of 1830 may be performed according to the methods described herein. In some examples, aspects of the operations of 1830 may be performed by a view processing engine as described with reference to FIGS. 13 through 16.

Figure 19:
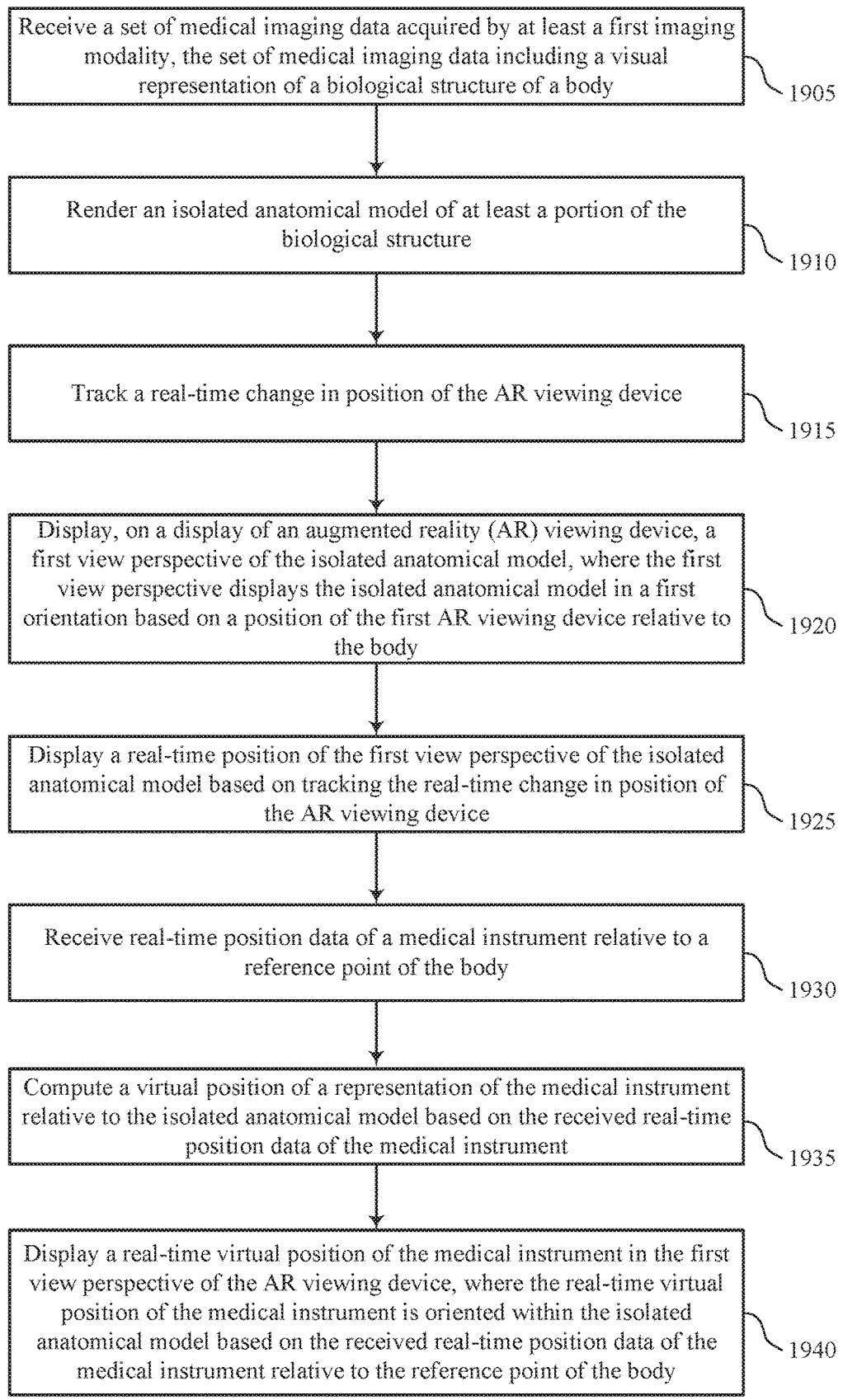

FIG. 19 shows a flowchart illustrating a method 1900 that supports medical device real-time rendering and referencing system in accordance with aspects of the present disclosure. The operations of method 1900 may be implemented by a medical data server or its components as described herein. For example, the operations of method 1900 may be performed by an augmented reality builder module as described with reference to FIGS. 13 through 16. In some examples, a medical data server may execute a set of instructions to control the functional elements of the medical data server to perform the functions described below. Additionally or alternatively, a medical data server may perform aspects of the functions described below using special-purpose hardware.

At 1905, the medical data server may receive a set of medical imaging data acquired by at least a first imaging modality, the set of medical imaging data including a visual representation of a biological structure of a body. The operations of 1905 may be performed according to the methods described herein. In some examples, aspects of the operations of 1905 may be performed by a medical imaging engine as described with reference to FIGS. 13 through 16.

At 1910, the medical data server may render an isolated anatomical model of at least a portion of the biological structure. The operations of 1910 may be performed according to the methods described herein. In some examples, aspects of the operations of 1910 may be performed by a rendering engine as described with reference to FIGS. 13 through 16.

At 1915, the medical data server may track a real-time change in position of the AR viewing device. The operations of 1915 may be performed according to the methods described herein. In some examples, aspects of the operations of 1915 may be performed by a view tracking component as described with reference to FIGS. 13 through 16.

At 1920, the medical data server may display, on a display of an augmented reality (AR) viewing device, a first view perspective of the isolated anatomical model, where the first view perspective displays the isolated anatomical model in a first orientation based on a position of the first AR viewing device relative to the body. The operations of 1920 may be performed according to the methods described herein. In some examples, aspects of the operations of 1920 may be performed by a view processing engine as described with reference to FIGS. 13 through 16.

At 1925, the medical data server may display a real-time position of the first view perspective of the isolated anatomical model based on tracking the real-time change in position of the AR viewing device. The operations of 1925 may be performed according to the methods described herein. In some examples, aspects of the operations of 1925 may be performed by a view processing engine as described with reference to FIGS. 13 through 16.

At 1930, the medical data server may receive real-time position data of a medical instrument relative to a reference point of the body. The operations of 1930 may be performed according to the methods described herein. In some examples, aspects of the operations of 1930 may be performed by an instrument tracking engine as described with reference to FIGS. 13 through 16.

At 1935, the medical data server may compute a virtual position of a representation of the medical instrument relative to the isolated anatomical model based on the received real-time position data of the medical instrument. The operations of 1935 may be performed according to the methods described herein. In some examples, aspects of the operations of 1935 may be performed by an instrument tracking engine as described with reference to FIGS. 13 through 16.

At 1940, the medical data server may display a real-time virtual position of the medical instrument in the first view perspective of the AR viewing device, where the real-time virtual position of the medical instrument is oriented within the isolated anatomical model based on the received real-time position data of the medical instrument relative to the reference point of the body. The operations of 1940 may be performed according to the methods described herein. In some examples, aspects of the operations of 1940 may be performed by an instrument visualization component as described with reference to FIGS. 13 through 16.

Figure 20:
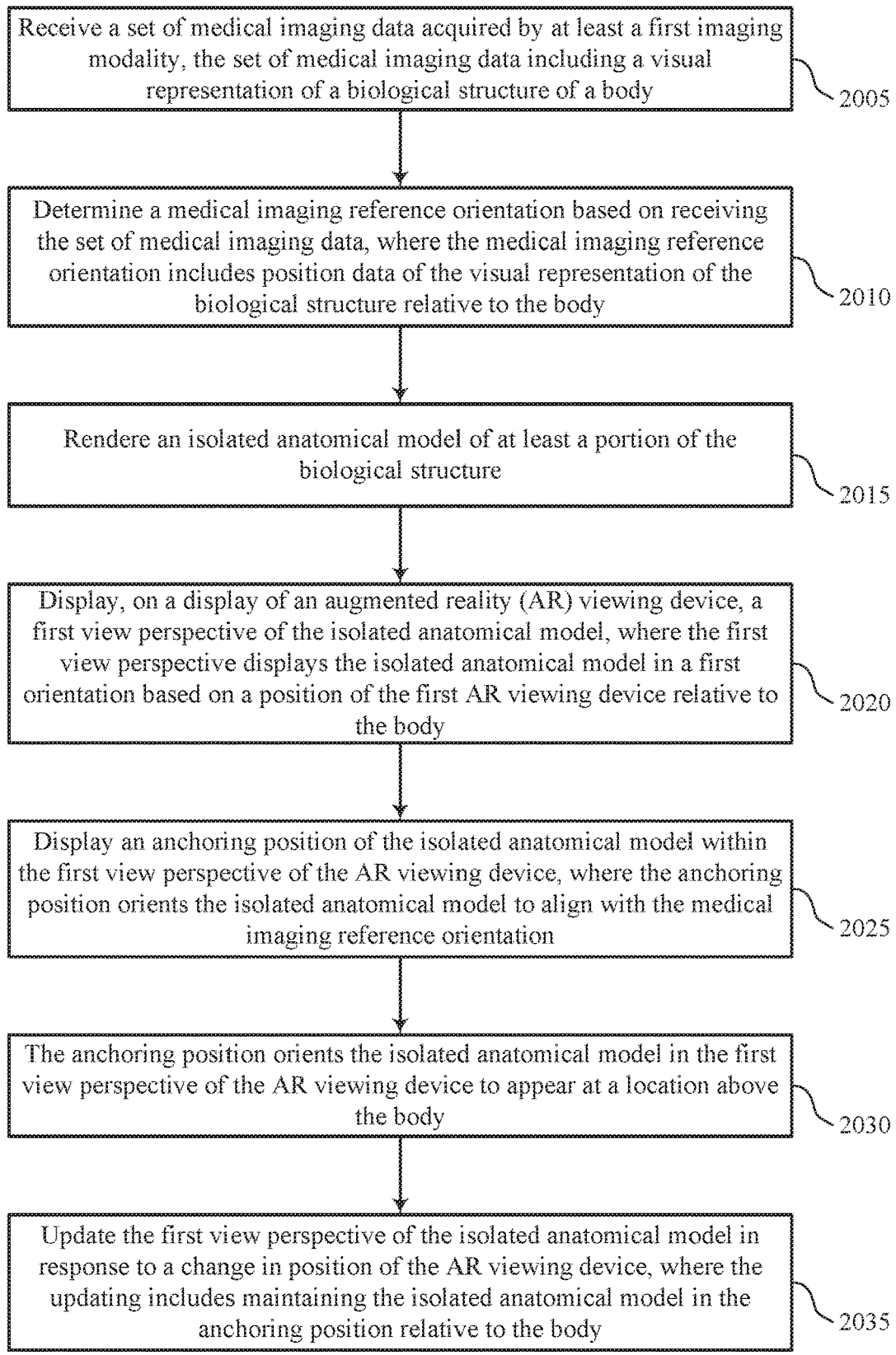

FIG. 20 shows a flowchart illustrating a method 2000 that supports medical device real-time rendering and referencing system in accordance with aspects of the present disclosure. The operations of method 2000 may be implemented by a medical data server or its components as described herein. For example, the operations of method 2000 may be performed by an augmented reality builder module as described with reference to FIGS. 13 through 16. In some examples, a medical data server may execute a set of instructions to control the functional elements of the medical data server to perform the functions described below. Additionally or alternatively, a medical data server may perform aspects of the functions described below using special-purpose hardware.

At 2005, the medical data server may receive a set of medical imaging data acquired by at least a first imaging modality, the set of medical imaging data including a visual representation of a biological structure of a body. The operations of 2005 may be performed according to the methods described herein. In some examples, aspects of the operations of 2005 may be performed by a medical imaging engine as described with reference to FIGS. 13 through 16.

At 2010, the medical data server may determine a medical imaging reference orientation based on receiving the set of medical imaging data, where the medical imaging reference orientation includes position data of the visual representation of the biological structure relative to the body. The operations of 2010 may be performed according to the methods described herein. In some examples, aspects of the operations of 2010 may be performed by a model referencing system as described with reference to FIGS. 13 through 16.

At 2015, the medical data server may render an isolated anatomical model of at least a portion of the biological structure. The operations of 2015 may be performed according to the methods described herein. In some examples, aspects of the operations of 2015 may be performed by a rendering engine as described with reference to FIGS. 13 through 16.

At 2020, the medical data server may display, on a display of an augmented reality (AR) viewing device, a first view perspective of the isolated anatomical model, where the first view perspective displays the isolated anatomical model in a first orientation based on a position of the first AR viewing device relative to the body. The operations of 2020 may be performed according to the methods described herein. In some examples, aspects of the operations of 2020 may be performed by a view processing engine as described with reference to FIGS. 13 through 16.

At 2025, the medical data server may display an anchoring position of the isolated anatomical model within the first view perspective of the AR viewing device, where the anchoring position orients the isolated anatomical model to align with the medical imaging reference orientation. The operations of 2025 may be performed according to the methods described herein. In some examples, aspects of the operations of 2025 may be performed by a view processing engine as described with reference to FIGS. 13 through 16.

At 2030, the medical data server may the anchoring position orients the isolated anatomical model in the first view perspective of the AR viewing device to appear at a location above the body. The operations of 2030 may be performed according to the methods described herein. In some examples, aspects of the operations of 2030 may be performed by a view processing engine as described with reference to FIGS. 13 through 16.

At 2035, the medical data server may update the first view perspective of the isolated anatomical model in response to a change in position of the AR viewing device, where the updating includes maintaining the isolated anatomical model in the anchoring position relative to the body. The operations of 2035 may be performed according to the methods described herein. In some examples, aspects of the operations of 2035 may be performed by a view processing engine as described with reference to FIGS. 13 through 16.

Figure 21:
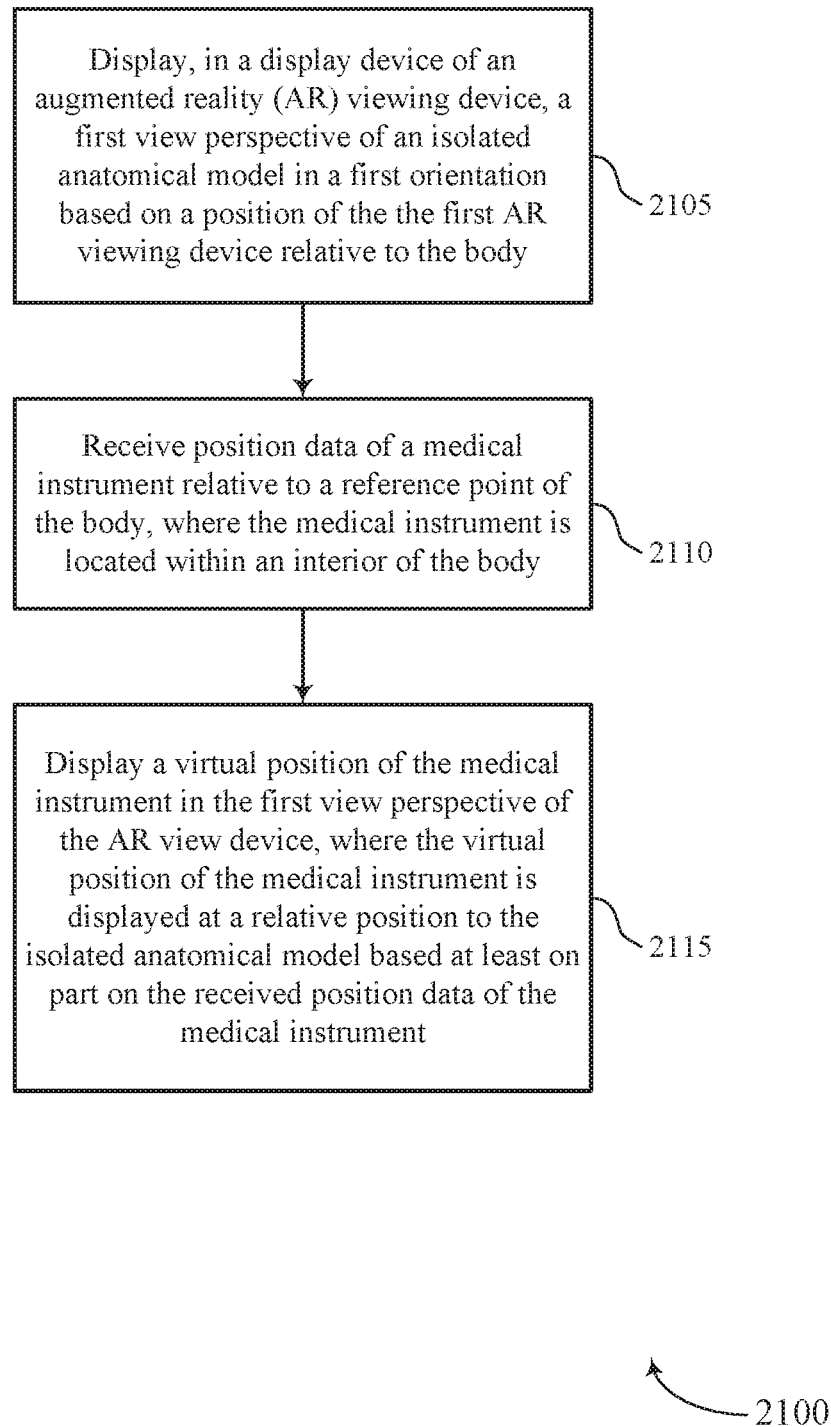

FIG. 21 shows a flowchart illustrating a method 2100 that supports medical device real-time rendering and referencing system in accordance with aspects of the present disclosure. The operations of method 2100 may be implemented by a medical data server or its components as described herein. For example, the operations of method 2100 may be performed by an augmented reality builder module as described with reference to FIGS. 13 through 16. In some examples, a medical data server may execute a set of instructions to control the functional elements of the medical data server to perform the functions described below. Additionally or alternatively, a medical data server may perform aspects of the functions described below using special-purpose hardware.

At 2105, the medical data server may display, in a display device of an augmented reality (AR) viewing device, a first view perspective of an isolated anatomical model in a first orientation based on a position of the first AR viewing device relative to the body. The operations of 2105 may be performed according to the methods described herein. In some examples, aspects of the operations of 2105 may be performed by a view processing engine as described with reference to FIGS. 13 through 16.

At 2110, the medical data server may receive position data of a medical instrument relative to a reference point of the body, where the medical instrument is located within an interior of the body. The operations of 2110 may be performed according to the methods described herein. In some examples, aspects of the operations of 2110 may be performed by an instrument tracking engine as described with reference to FIGS. 13 through 16.

At 2115, the medical data server may display a virtual position of the medical instrument in the first view perspective of the AR view device, where the virtual position of the medical instrument is displayed at a relative position to the isolated anatomical model based at least on part on the received position data of the medical instrument. The operations of 2115 may be performed according to the methods described herein. In some examples, aspects of the operations of 2115 may be performed by an instrument visualization component as described with reference to FIGS. 13 through 16.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B. or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for medical imaging, the method comprising:
   receiving a set of medical imaging data acquired by at least a first imaging modality, the set of medical imaging data comprising a visual representation of a biological structure of a body;
   rendering an anatomical model of at least a portion of the biological structure, wherein the rendering comprises:
      generating a contrasted image of the anatomical model by darkening the biological structure and lightening image noise after receiving the set of medical imaging data;
      vectorizing the contrasted image of the anatomical model to refine edges of the biological structure after generating the contrasted image; and
      removing the image noise from the vectorized contrasted image to render an isolated anatomical model after vectorizing the contrasted image; and
   displaying, on a display of an augmented reality (AR) viewing device, a first view perspective of the isolated anatomical model, wherein the first view perspective displays the isolated anatomical model in a first orientation based at least in part on a position of the first AR viewing device relative to the body.

2. The method of claim 1, further comprising:
   tracking a real-time change in position of the AR viewing device; and
   displaying a real-time position of the first view perspective of the isolated anatomical model based at least in part on tracking the real-time change in position of the AR viewing device.

3. The method of claim 2, wherein displaying the real-time position of the first view perspective of the isolated anatomical model comprises:
   updating the first view perspective of the isolated anatomical model based at least in part on a change in position of the AR viewing device relative to the body, wherein updating the first view perspective comprises displaying the isolated anatomical model in a second orientation based at least in part on the change in position of the AR viewing device.

4. The method of claim 2, further comprising:
   receiving real-time position data of a medical instrument relative to a reference point of the body.

5. The method of claim 4, further comprising:
   computing a virtual position of the medical instrument relative to the isolated anatomical model based at least in part on the received real-time position data of the medical instrument.

6. The method of claim 5, wherein the computing the virtual position of the medical instrument corresponds to a real-time position of the medical instrument relative to the reference point of the body.

7. The method of claim 4, further comprising:
   displaying a virtual position of the medical instrument in the first view perspective of the AR viewing device, wherein the virtual position of the medical instrument is oriented within the isolated anatomical model based at least in part on the received real-time position data of the medical instrument relative to the reference point of the body.

8. The method of claim 4, wherein receiving the real-time position data of the medical instrument further comprises:
   receiving signal data from an active tracking component located on the medical instrument.

9. The method of claim 8, wherein the signal data comprises at least one of a force measurement, an ultrasonic measurement, a magnetic measurement, an orientation measurement, or a combination thereof.

10. The method of claim 8, further comprising:
receiving at least a portion of the real-time position data of the medical instrument from a navigation instrument located outside the body.

11. The method of claim 10, wherein the real-time position data of the medical instrument comprises at least one of ultrasonic data, radio frequency identification (RFID) sensor data, contrast imaging data, global positioning system (GPS) data, orientation data, or a combination thereof.

12. The method of claim 1, further comprising:
determining a medical imaging reference orientation based at least in part on receiving the set of medical imaging data, wherein the medical imaging reference orientation comprises position data of the visual representation of the biological structure relative to the body; and
displaying an anchoring orientation of the isolated anatomical model within the first view perspective of the AR viewing device, wherein the anchoring orientation positions the isolated anatomical model to align with the medical imaging reference orientation.

13. The method of claim 12, wherein the anchoring orientation positions the isolated anatomical model in the first view perspective of the AR viewing device to appear at a location above the body.

14. The method of claim 13, further comprising:
updating the first view perspective of the isolated anatomical model in response to a change in position of the AR viewing device, wherein the updating comprises maintaining the isolated anatomical model in the anchoring orientation relative to the body.

15. The method of claim 12, further comprising:
receiving a command to change an orientation of the isolated anatomical model from the anchoring orientation to a selected orientation; and
displaying, on the display the AR viewing device, a second orientation of the isolated anatomical model, wherein the second orientation of the isolated anatomical model displays the isolated anatomical model at the selected orientation based at least in part on the position of the AR viewing device relative to the body.

16. The method of claim 1, further comprising:
displaying, on a display of a second AR viewing device, a second view perspective of the isolated anatomical model, wherein the second view perspective displays the isolated anatomical model in a second orientation based at least in part on a position of the second AR viewing device relative to the body.

17. A method for image rendering, the method comprising:
receiving a set of imaging data acquired by at least a first imaging modality, the set of imaging data comprising a visual representation of a structure;
rendering a model of at least a portion of the structure, wherein the rendering comprises:
generating a contrasted image of the model by darkening the structure and lightening image noise after receiving the set of imaging data;
vectorizing the contrasted image of the model to refine edges of the structure after generating the contrasted image; and
removing the image noise from the vectorized contrasted image to render an isolated model after vectorizing the contrasted image; and displaying, on a display of an augmented reality (AR) viewing device, a first view perspective of the isolated model, wherein the first view perspective displays the isolated model in a first orientation based at least in part on a position of the first AR viewing device relative to viewing reference point.

18. The method of claim 17, wherein:
the structure comprises at least a set of internal features that are contained within the interior of the structure; and
the set of imaging data comprises a visual representation of at least a portion of the set of internal features.

19. An apparatus for medical imaging comprising:
a processor;
memory in electronic communication with the processor; and
instructions stored in the memory and executable by the processor to cause the apparatus to:
receive a set of medical imaging data acquired by at least a first imaging modality, the set of medical imaging data comprising a visual representation of a biological structure of a body;
rendering an anatomical model of at least a portion of the biological structure, wherein the rendering comprises:
generating a contrasted image of the anatomical model by darkening the biological structure and lightening image noise after receiving the set of medical imaging data;
vectorizing the contrasted image of the anatomical model to refine edges of the biological structure after generating the contrasted image; and
removing the image noise from the vectorized contrasted image to render an isolated anatomical model after vectorizing the contrasted image; and
display, on a display of an augmented reality (AR) viewing device, a first view perspective of the isolated anatomical model, wherein the first view perspective displays the isolated anatomical model in a first orientation based at least in part on a position of the first AR viewing device relative to the body.

20. The apparatus of claim 19, wherein the instructions are further executable by the processor to cause the apparatus to:
track a real-time change in position of the AR viewing device; and
display a real-time position of the first view perspective of the isolated anatomical model based at least in part on tracking the real-time change in position of the AR viewing device.

21. The apparatus of claim 20, wherein the instructions to display the real-time position of the first view perspective of the isolated anatomical model are executable by the processor to cause the apparatus to:
update the first view perspective of the isolated anatomical model based at least in part on a change in position of the AR viewing device relative to the body, and wherein updating the first view perspective causes the apparatus to display the isolated anatomical model in a second orientation based at least in part on the change in position of the AR viewing device.

22. The apparatus of claim 20, wherein the instructions are further executable by the processor to cause the apparatus to:
receive real-time position data of a medical instrument relative to a reference point of the body.

23. The apparatus of claim 22, wherein the instructions are further executable by the processor to cause the apparatus to:
compute a virtual position of the medical instrument relative to the isolated anatomical model based at least in part on the received real-time position data of the medical instrument.

24. The apparatus of claim 23, wherein the computing the virtual position of the medical instrument corresponds to a real-time position of the medical instrument relative to the reference point of the body.

25. The apparatus of claim 22, wherein the instructions are further executable by the processor to cause the apparatus to:
display a virtual position of the medical instrument in the first view perspective of the AR viewing device, and wherein the virtual position of the medical instrument is oriented within the isolated anatomical model based at least in part on the received real-time position data of the medical instrument relative to the reference point of the body.

26. The apparatus of claim 22, wherein the instructions to receive the real-time position data of the medical instrument are further executable by the processor to cause the apparatus to:
receive signal data from an active tracking component located on the medical instrument.

27. The apparatus of claim 26, wherein the instructions are further executable by the processor to cause the apparatus to:
receive at least a portion of the real-time position data of the medical instrument from a navigation instrument located outside the body.

28. The apparatus of claim 19, wherein the instructions are further executable by the processor to cause the apparatus to:
determine a medical imaging reference orientation based at least in part on receiving the set of medical imaging data, wherein the medical imaging reference orientation comprises position data of the visual representation of the biological structure relative to the body; and
display an anchoring orientation of the isolated anatomical model within the first view perspective of the AR viewing device, wherein the anchoring orientation positions the isolated anatomical model to align with the medical imaging reference orientation.

29. The apparatus of claim 28, wherein the anchoring orientation positions the isolated anatomical model in the first view perspective of the AR viewing device to appear at a location above the body.

30. The apparatus of claim 29, wherein the instructions are further executable by the processor to cause the apparatus to:
update the first view perspective of the isolated anatomical model in response to a change in position of the AR viewing device, and wherein the updating is executable by the processor to cause the apparatus to maintain the isolated anatomical model in the anchoring orientation relative to the body.

31. The apparatus of claim 28, wherein the instructions are further executable by the processor to cause the apparatus to:
receive a command to change an orientation of the isolated anatomical model from the anchoring orientation to a selected orientation; and
display, on the display of the AR viewing device, a second orientation of the isolated anatomical model, wherein the second orientation of the isolated anatomical model displays the isolated anatomical model at the selected orientation based at least in part on the position of the AR viewing device relative to the body.

32. A method for medical imaging, comprising:
rendering an anatomical model of at least a portion of a biological structure, wherein the rendering comprises:
generating a contrasted image of the anatomical model by darkening the biological structure and lightening image noise after receiving a set of medical imaging data;
vectorizing the contrasted image of the anatomical model to refine edges of the biological structure after generating the contrasted image; and
removing the image noise from the vectorized contrasted image to render an isolated anatomical model after vectorizing the contrasted image;
displaying, in a display device of an augmented reality (AR) viewing device, a first view perspective of the isolated anatomical model in a first orientation based at least in part on a position of the first AR viewing device relative to a body;
receiving position data of a medical instrument relative to a reference point of the body, wherein the medical instrument is located within an interior of the body; and
displaying a virtual position of the medical instrument in the first view perspective of the AR viewing device, wherein the virtual position of the medical instrument is displayed at a relative position to the isolated anatomical model based at least on part on the received position data of the medical instrument.

* * * * *